(12) United States Patent
Matsuda et al.

(10) Patent No.: US 7,402,413 B2
(45) Date of Patent: Jul. 22, 2008

(54) METHOD OF EXPRESSING LONG-CHAIN PRENYL DIPHOSPHATE SYNTHASE

(75) Inventors: Hideyuki Matsuda, Shimane (JP);
Makoto Kawamukai, Shimane (JP);
Kazuyoshi Yajima, Hyogo (JP)

(73) Assignee: Kaneka Corporation, Osaka (JP)

( * ) Notice: Subject to any disclaimer, the term of this patent is extended or adjusted under 35 U.S.C. 154(b) by 478 days.

(21) Appl. No.: 10/477,269

(22) PCT Filed: May 10, 2002

(86) PCT No.: PCT/JP02/04566

§ 371 (c)(1),
(2), (4) Date: Mar. 19, 2004

(87) PCT Pub. No.: WO02/092811

PCT Pub. Date: Nov. 21, 2002

(65) Prior Publication Data
US 2004/0137567 A1    Jul. 15, 2004

(30) Foreign Application Priority Data
May 11, 2001    (JP)    .............................. 2001-140977

(51) Int. Cl.
*C12P 7/66*    (2006.01)
*C12N 15/12*    (2006.01)
*C12N 1/21*    (2006.01)
(52) U.S. Cl. ............... 435/133; 435/252.3; 435/252.33; 435/320.1; 536/23.5
(58) Field of Classification Search ........................ None
See application file for complete search history.

(56) References Cited

U.S. PATENT DOCUMENTS

| 6,225,097 B1 | 5/2001 | Obata et al. | |
|---|---|---|---|
| 6,762,037 B1 * | 7/2004 | Matsuda et al. | ............ 435/68.1 |
| 6,783,969 B1 * | 8/2004 | Tang et al. | ................. 435/219 |

FOREIGN PATENT DOCUMENTS

| EP | 1 123 979 A1 | 8/2001 |
|---|---|---|
| JP | 9-173076 | 7/1997 |
| JP | 10-57072 | 3/1998 |
| JP | 11-178590 A1 | 7/1999 |
| JP | 2001-61478 A | 3/2001 |
| JP | 2002-191367 A | 7/2002 |
| WO | WO 01/14567 A1 | 3/2001 |
| WO | WO 02/40682 A1 | 5/2002 |
| WO | WO 02/052017 A1 | 7/2002 |
| WO | WO 02/070539 A2 | 9/2002 |
| WO | WO 02/070539 A3 | 9/2002 |
| WO | WO 02/088365 A1 | 11/2002 |

OTHER PUBLICATIONS

Sequence Search, US 6,762,037.*
Sequence Search, US 6,225,097.*
Ashby, M.N., et al. (1990) J. Biol. Chem. 265 (22), 13157-13164.*
J. Choi et al. "Biotechnological Production and Applications of Coenzyme Q10", Appl. Microbiol. Biotechnol. 68: 9-15 (2005).*
Suzuki, K., et al. "Analysis of the Decaprenyl Diphosphate Synthase (*dps*) Gene in Fission Yeast Suggests a Role of Ubiquinone as an Antioxidant", *J. Biochem.*, Mar. 1997, vol. 121, No. 3, pp. 496-505.
Okada, K., et al. "Cloning of the *sdsA* Gene Encoding Solanesyl Diphosphate Synthase from *Rhodobacter capsulatus* and Its Functional Expression in *Escherichia coli* and *Saccharomyces cerevisiae*", *J. Bacteriol*, Oct. 1997, vol. 179, No. 19, pp. 5992-5998.
Okada, K., et al. "Molecular Cloning and Mutational Analysis of the *ddsA* Gene Encoding Decaprenyl Diphosphate Synthase From *Gluconobacter suboxydans*", *Eur. J. Biochem.*, Apr. 1998, vol. 255, pp. 52-59.
International Search Report from Corresponding PCT Application No. PCT/JP02/04566, Dated Sep. 4, 2002, 2 (double-sided) pages.
Patent Cooperation Treaty PCT International Preliminary Examination Report (PCT Article 36 and Rule 70), From Corresponding International Application No. PCT/JP02/04566, Dated May 8, 2003, 7 Pages.
Supplementary Partial European Search Report from Application No. EP 02 76 9565, Jan. 3, 2005, 7 pages.
Saiki, Ryoichi et al., "Fission Yeast Decaprenyl Diphosphate Synthase Consists of Dps1 and the Newly Characterized Dlp1 Protein in a Novel Heterotetrameric Structure," *Eur. J. Biochem.*, vol. 270, No. 20, Oct. 2003, pp. 4113-4121 (XP002306286).
Wood, V. et al., "The Genome Sequence of Schizosaccharomyces Pombe," *Nature*, vol. 415, No. 6874, Feb. 21, 2002, pp. 871-880 (XP002306285).
Kainou, Tomohiro et al., "Dimer Formation of Octaprenyl-diphosphate Synthase (IspB) Is Essential for Chain Length Determination of Ubiquinone," *The Journal of Biological Chemistry*, vol. 276, No. 11, Mar. 16, 2001, pp. 7876-7883 (XP002306314).

(Continued)

*Primary Examiner*—Rebecca Prouty
(74) *Attorney, Agent, or Firm*—Brinks Hofer Gilson & Lione

(57) ABSTRACT

The present invention provides a method of producing a long-chain prenyl diphosphate synthase (in particular decaprenyl diphosphate synthase and solanesyl diphosphate synthase) using a gene and a protein which are required for enabling or enhancing the activity expression of a eukaryote-derived long-chain prenyl diphosphate synthase as well as a method of efficiently producing a coenzyme Q having a long-chain isoprenoid in its side chain (in particular coenzyme $Q_9$ or coenzyme $Q_{10}$) using a microorganism. The present invention relates to a DNA having a base sequence shown under SEQ ID NO:1, 3 or 5 and a DNA sequence derived from the above base sequence by deletion, addition, insertion and/or substitution of one to several bases thereof, and coding for a protein enabling (functioning) or enhancing the activity expression of a eukaryote-derived long-chain prenyl diphosphate synthase in a host microorganism.

7 Claims, 5 Drawing Sheets

OTHER PUBLICATIONS

"Coq1 Protein (Spac19g12.12 Protein) (Decaprenyl Diphosphate Synthase Subunit 2)," Jan. 1, 1998, retrieved from EBI Database Accession No. 013851 (XP002306116).

"S.pombe Chromosome I Cosmid c19G12," Jul. 1, 1997, retrieved from EBI Database Accession No. Z97209 CDS 26025—26909 (XP002306115).

Ogura, Kyozo et al., "Polyprenyl Diphosphate Synthases," *Subcellular Biochemistry*, vol. 28, 1997, pp. 57-87 (XP009040275).

Okada, Kazunori et al., "Polyprenyl Diphosphate Synthase Essentially Defines the Length of the Side Chain of Ubiquinone," *Biochimica-et-Biophysica-Acta*, vol. 1302, No. 3, 1996, pp. 217-223 (XP002306281).

"*Homo sapiens* Candidate Tumor Suppressor Protein mRNA, Complete CDS," Aug. 8, 2000, retrieved from EBI, Database Accession No. AF254956 (XP002319217).

"Candidate Tumor Suppressor Protein," Oct. 1, 2000, Retrieved from EBI, Database Accession No. Q9NR58 (XP002319218).

Supplementary European Search Report from Application No. EP 02 76 9565, Mar. 1, 2005, 8 pages.

'Hypothetical protein SPAC19G12.12 - fission yeast (Schizosaccharomyces pombe), 'Protein Database (online), National Center for Biotechnology Information, National Library of Medicine, Dec. 3, 1999.

* cited by examiner

CoQ10 standard

E. coli DH5 α

E. coli DH5 α (pSTVDLP1)

E. coli DH5 α (pBSDPS)

E. coli DH5 α (pSTVDLP1, pBSDPS)

SEQUENCE LISTING

<160> NUMBER OF SEQ ID NOS: 18

<210> SEQ ID NO 1
<211> LENGTH: 885
<212> TYPE: DNA
<213> ORGANISM: Schizosaccharomyces pombe

<400> SEQUENCE: 1

| atg | agc | ttt | ccg | ttc | gct | agt | ttg | ctg | aaa | agg | cct | tct | gca | ata | agc | 48 |
|---|---|---|---|---|---|---|---|---|---|---|---|---|---|---|---|---|
| Met | Ser | Phe | Pro | Phe | Ala | Ser | Leu | Leu | Lys | Arg | Pro | Ser | Ala | Ile | Ser | |
| 1 | | | | 5 | | | | | 10 | | | | | 15 | | |

| tct | cta | tta | tct | tta | aaa | aaa | cct | ggt | tcc | tgg | tct | tcc | att | ctg | cta | 96 |
|---|---|---|---|---|---|---|---|---|---|---|---|---|---|---|---|---|
| Ser | Leu | Leu | Ser | Leu | Lys | Lys | Pro | Gly | Ser | Trp | Ser | Ser | Ile | Leu | Leu | |
| | | | 20 | | | | | 25 | | | | | 30 | | | |

| aaa | gct | gta | ggg | gtt | tta | tca | cga | gat | tcc | cgt | tgg | cat | tct | gac | tta | 144 |
|---|---|---|---|---|---|---|---|---|---|---|---|---|---|---|---|---|
| Lys | Ala | Val | Gly | Val | Leu | Ser | Arg | Asp | Ser | Arg | Trp | His | Ser | Asp | Leu | |
| | | 35 | | | | | 40 | | | | | 45 | | | | |

| tta | aaa | atg | ctt | aca | gaa | gaa | atg | gat | tct | tta | aat | ggt | caa | att | aat | 192 |
|---|---|---|---|---|---|---|---|---|---|---|---|---|---|---|---|---|
| Leu | Lys | Met | Leu | Thr | Glu | Glu | Met | Asp | Ser | Leu | Asn | Gly | Gln | Ile | Asn | |
| 50 | | | | | 55 | | | | | 60 | | | | | | |

| acg | tgg | aca | gat | aat | aat | cct | tta | tta | gat | gaa | att | acg | aag | cca | tac | 240 |
|---|---|---|---|---|---|---|---|---|---|---|---|---|---|---|---|---|
| Thr | Trp | Thr | Asp | Asn | Asn | Pro | Leu | Leu | Asp | Glu | Ile | Thr | Lys | Pro | Tyr | |
| 65 | | | | | 70 | | | | | 75 | | | | | 80 | |

| aga | aaa | tct | tca | act | cgt | ttt | ttt | cat | ccg | ctt | ctt | gta | ctt | cta | atg | 288 |
|---|---|---|---|---|---|---|---|---|---|---|---|---|---|---|---|---|
| Arg | Lys | Ser | Ser | Thr | Arg | Phe | Phe | His | Pro | Leu | Leu | Val | Leu | Leu | Met | |
| | | | | 85 | | | | | 90 | | | | | 95 | | |

| tct | aga | gca | tca | gta | aat | ggg | gat | cca | ccg | agt | cag | caa | cta | ttt | caa | 336 |
|---|---|---|---|---|---|---|---|---|---|---|---|---|---|---|---|---|
| Ser | Arg | Ala | Ser | Val | Asn | Gly | Asp | Pro | Pro | Ser | Gln | Gln | Leu | Phe | Gln | |
| | | | 100 | | | | | 105 | | | | | 110 | | | |

| agg | tac | aaa | caa | ctt | gcc | cgt | gta | aca | gaa | ttg | att | cat | gct | gcc | aat | 384 |
|---|---|---|---|---|---|---|---|---|---|---|---|---|---|---|---|---|
| Arg | Tyr | Lys | Gln | Leu | Ala | Arg | Val | Thr | Glu | Leu | Ile | His | Ala | Ala | Asn | |
| | | 115 | | | | | 120 | | | | | 125 | | | | |

| ata | att | cat | att | aat | att | gga | gaa | gaa | caa | agc | aac | gaa | cag | att | aaa | 432 |
|---|---|---|---|---|---|---|---|---|---|---|---|---|---|---|---|---|
| Ile | Ile | His | Ile | Asn | Ile | Gly | Glu | Glu | Gln | Ser | Asn | Glu | Gln | Ile | Lys | |
| 130 | | | | | 135 | | | | | 140 | | | | | | |

| ctt | gca | acg | ttg | gtt | gga | gat | tat | tta | ctc | gga | aag | gcg | tct | gtt | gat | 480 |
|---|---|---|---|---|---|---|---|---|---|---|---|---|---|---|---|---|
| Leu | Ala | Thr | Leu | Val | Gly | Asp | Tyr | Leu | Leu | Gly | Lys | Ala | Ser | Val | Asp | |
| 145 | | | | | 150 | | | | | 155 | | | | | 160 | |

| tta | gca | cat | tta | gaa | aac | aac | gct | att | aca | gaa | att | atg | gct | tct | gtt | 528 |
|---|---|---|---|---|---|---|---|---|---|---|---|---|---|---|---|---|
| Leu | Ala | His | Leu | Glu | Asn | Asn | Ala | Ile | Thr | Glu | Ile | Met | Ala | Ser | Val | |
| | | | | 165 | | | | | 170 | | | | | 175 | | |

| att | gca | aac | tta | gtt | gaa | ggg | cac | ttc | gga | agc | cga | caa | aat | ggc | tct | 576 |
|---|---|---|---|---|---|---|---|---|---|---|---|---|---|---|---|---|
| Ile | Ala | Asn | Leu | Val | Glu | Gly | His | Phe | Gly | Ser | Arg | Gln | Asn | Gly | Ser | |
| | | | 180 | | | | | 185 | | | | | 190 | | | |

| gtt | ggt | ttg | tca | aac | gaa | cga | acc | atc | ctt | ctg | caa | tca | gcc | ttt | atg | 624 |
|---|---|---|---|---|---|---|---|---|---|---|---|---|---|---|---|---|
| Val | Gly | Leu | Ser | Asn | Glu | Arg | Thr | Ile | Leu | Leu | Gln | Ser | Ala | Phe | Met | |
| | | 195 | | | | | 200 | | | | | 205 | | | | |

| cca | gca | aag | gca | tgt | tta | tgc | gca | agc | ata | ttg | aat | aac | tca | tca | caa | 672 |
|---|---|---|---|---|---|---|---|---|---|---|---|---|---|---|---|---|
| Pro | Ala | Lys | Ala | Cys | Leu | Cys | Ala | Ser | Ile | Leu | Asn | Asn | Ser | Ser | Gln | |
| | 210 | | | | | 215 | | | | | 220 | | | | | |

| tac | att | aat | gat | gcg | tgt | ttc | aat | tat | gga | aaa | ttt | cta | ggc | tta | tcg | 720 |
|---|---|---|---|---|---|---|---|---|---|---|---|---|---|---|---|---|
| Tyr | Ile | Asn | Asp | Ala | Cys | Phe | Asn | Tyr | Gly | Lys | Phe | Leu | Gly | Leu | Ser | |
| 225 | | | | | 230 | | | | | 235 | | | | | 240 | |

| ctg | caa | ctg | gcc | cat | aag | cct | gta | tct | cct | gac | gcc | caa | gtt | ttg | caa | 768 |
|---|---|---|---|---|---|---|---|---|---|---|---|---|---|---|---|---|
| Leu | Gln | Leu | Ala | His | Lys | Pro | Val | Ser | Pro | Asp | Ala | Gln | Val | Leu | Gln | |
| | | | | 245 | | | | | 250 | | | | | 255 | | |

| aag | aat | aat | gac | att | ttg | aaa | aca | tat | gtt | gag | aat | gcc | aag | agc | tca | 816 |
|---|---|---|---|---|---|---|---|---|---|---|---|---|---|---|---|---|
| Lys | Asn | Asn | Asp | Ile | Leu | Lys | Thr | Tyr | Val | Glu | Asn | Ala | Lys | Ser | Ser | |
| | | | 260 | | | | | 265 | | | | | 270 | | | |

```
ttg tct gtt ttc ccc gat ata gag gct aag caa gct ctc atg gaa atc    864
Leu Ser Val Phe Pro Asp Ile Glu Ala Lys Gln Ala Leu Met Glu Ile
    275                 280                 285 gct aat agt gtt tcg aag taa                                        885
Ala Asn Ser Val Ser Lys
    290

<210> SEQ ID NO 2
<211> LENGTH: 294
<212> TYPE: PRT
<213> ORGANISM: Schizosaccharomyces pombe

<400> SEQUENCE: 2

Met Ser Phe Pro Phe Ala Ser Leu Leu Lys Arg Pro Ser Ala Ile Ser
  1               5                  10                  15

Ser Leu Leu Ser Leu Lys Lys Pro Gly Ser Trp Ser Ile Leu Leu
             20                  25                  30

Lys Ala Val Gly Val Leu Ser Arg Asp Ser Arg Trp His Ser Asp Leu
         35                  40                  45

Leu Lys Met Leu Thr Glu Glu Met Asp Ser Leu Asn Gly Gln Ile Asn
     50                  55                  60

Thr Trp Thr Asp Asn Asn Pro Leu Leu Asp Glu Ile Thr Lys Pro Tyr
 65                  70                  75                  80

Arg Lys Ser Ser Thr Arg Phe Phe His Pro Leu Leu Val Leu Leu Met
                 85                  90                  95

Ser Arg Ala Ser Val Asn Gly Asp Pro Pro Ser Gln Gln Leu Phe Gln
            100                 105                 110

Arg Tyr Lys Gln Leu Ala Arg Val Thr Glu Leu Ile His Ala Ala Asn
        115                 120                 125

Ile Ile His Ile Asn Ile Gly Glu Glu Gln Ser Asn Glu Gln Ile Lys
    130                 135                 140

Leu Ala Thr Leu Val Gly Asp Tyr Leu Leu Gly Lys Ala Ser Val Asp
145                 150                 155                 160

Leu Ala His Leu Glu Asn Asn Ala Ile Thr Glu Ile Met Ala Ser Val
                165                 170                 175

Ile Ala Asn Leu Val Glu Gly His Phe Gly Ser Arg Gln Asn Gly Ser
            180                 185                 190

Val Gly Leu Ser Asn Glu Arg Thr Ile Leu Leu Gln Ser Ala Phe Met
        195                 200                 205

Pro Ala Lys Ala Cys Leu Cys Ala Ser Ile Leu Asn Asn Ser Ser Gln
    210                 215                 220

Tyr Ile Asn Asp Ala Cys Phe Asn Tyr Gly Lys Phe Leu Gly Leu Ser
225                 230                 235                 240

Leu Gln Leu Ala His Lys Pro Val Ser Pro Asp Ala Gln Val Leu Gln
                245                 250                 255

Lys Asn Asn Asp Ile Leu Lys Thr Tyr Val Glu Asn Ala Lys Ser Ser
            260                 265                 270

Leu Ser Val Phe Pro Asp Ile Glu Ala Lys Gln Ala Leu Met Glu Ile
        275                 280                 285

Ala Asn Ser Val Ser Lys
    290

<210> SEQ ID NO 3
<211> LENGTH: 1200
<212> TYPE: DNA
<213> ORGANISM: human
```

<400> SEQUENCE: 3

| | | | | | | | | | | | | | | | | |
|---|---|---|---|---|---|---|---|---|---|---|---|---|---|---|---|---|
| atg | aac | ttt | cgg | cag | ctg | ctg | ttg | cac | ttg | cca | cgt | tat | ctt | gga | gcc | 48 |
| Met | Asn | Phe | Arg | Gln | Leu | Leu | Leu | His | Leu | Pro | Arg | Tyr | Leu | Gly | Ala | |
| 1 | | | | 5 | | | | | 10 | | | | | 15 | | |

| tcg | ggt | tcc | ccg | cgt | cgc | ctg | tgg | tgg | tcc | ccg | tcc | ctc | gac | acc | atc | 96 |
|---|---|---|---|---|---|---|---|---|---|---|---|---|---|---|---|---|
| Ser | Gly | Ser | Pro | Arg | Arg | Leu | Trp | Trp | Ser | Pro | Ser | Leu | Asp | Thr | Ile | |
| | | | 20 | | | | | 25 | | | | | 30 | | | |

| tcc | tcg | gtg | ggc | tct | tgg | cgt | ggt | cgg | tcc | tcc | aag | tcc | ccg | gcc | cac | 144 |
|---|---|---|---|---|---|---|---|---|---|---|---|---|---|---|---|---|
| Ser | Ser | Val | Gly | Ser | Trp | Arg | Gly | Arg | Ser | Ser | Lys | Ser | Pro | Ala | His | |
| | | 35 | | | | | 40 | | | | | 45 | | | | |

| tgg | aat | cag | gta | gtg | tca | gag | gcg | gag | aag | atc | gtg | ggg | tac | ccc | acg | 192 |
|---|---|---|---|---|---|---|---|---|---|---|---|---|---|---|---|---|
| Trp | Asn | Gln | Val | Val | Ser | Glu | Ala | Glu | Lys | Ile | Val | Gly | Tyr | Pro | Thr | |
| 50 | | | | | 55 | | | | | 60 | | | | | | |

| tcc | ttc | atg | agc | ctt | cgc | tgc | ctg | ctg | agc | gac | gag | ctc | agc | aac | atc | 240 |
|---|---|---|---|---|---|---|---|---|---|---|---|---|---|---|---|---|
| Ser | Phe | Met | Ser | Leu | Arg | Cys | Leu | Leu | Ser | Asp | Glu | Leu | Ser | Asn | Ile | |
| 65 | | | | 70 | | | | | 75 | | | | | 80 | | |

| gct | atg | cag | gtg | cgg | aag | ctg | gtg | ggc | act | cag | cac | cct | ctg | ctt | acc | 288 |
|---|---|---|---|---|---|---|---|---|---|---|---|---|---|---|---|---|
| Ala | Met | Gln | Val | Arg | Lys | Leu | Val | Gly | Thr | Gln | His | Pro | Leu | Leu | Thr | |
| | | | 85 | | | | | 90 | | | | | 95 | | | |

| aca | gcc | agg | ggg | ctt | gta | cat | gac | agc | tgg | aat | agc | ctc | cag | ttg | agg | 336 |
|---|---|---|---|---|---|---|---|---|---|---|---|---|---|---|---|---|
| Thr | Ala | Arg | Gly | Leu | Val | His | Asp | Ser | Trp | Asn | Ser | Leu | Gln | Leu | Arg | |
| | | 100 | | | | | 105 | | | | | 110 | | | | |

| ggc | ttg | gtg | gtg | ctc | ctt | atc | tct | aaa | gca | gct | ggg | ccc | agc | agc | gtg | 384 |
|---|---|---|---|---|---|---|---|---|---|---|---|---|---|---|---|---|
| Gly | Leu | Val | Val | Leu | Leu | Ile | Ser | Lys | Ala | Ala | Gly | Pro | Ser | Ser | Val | |
| | | 115 | | | | | 120 | | | | | 125 | | | | |

| aac | act | tca | tgt | cag | aac | tat | gac | atg | gtc | agt | ggg | atc | tac | tca | tgt | 432 |
|---|---|---|---|---|---|---|---|---|---|---|---|---|---|---|---|---|
| Asn | Thr | Ser | Cys | Gln | Asn | Tyr | Asp | Met | Val | Ser | Gly | Ile | Tyr | Ser | Cys | |
| | 130 | | | | | 135 | | | | | 140 | | | | | |

| caa | aga | agt | ttg | gca | gag | atc | acg | gag | cta | att | cat | att | gct | ctc | ctt | 480 |
|---|---|---|---|---|---|---|---|---|---|---|---|---|---|---|---|---|
| Gln | Arg | Ser | Leu | Ala | Glu | Ile | Thr | Glu | Leu | Ile | His | Ile | Ala | Leu | Leu | |
| 145 | | | | | 150 | | | | | 155 | | | | | 160 | |

| gta | cat | cgt | ggg | ata | gta | aat | tta | aat | gag | ttg | caa | tca | tct | gat | ggt | 528 |
|---|---|---|---|---|---|---|---|---|---|---|---|---|---|---|---|---|
| Val | His | Arg | Gly | Ile | Val | Asn | Leu | Asn | Glu | Leu | Gln | Ser | Ser | Asp | Gly | |
| | | | 165 | | | | | 170 | | | | | 175 | | | |

| cca | ctg | aaa | gac | atg | caa | ttt | gga | aat | aaa | att | gct | atc | ctg | agt | gga | 576 |
|---|---|---|---|---|---|---|---|---|---|---|---|---|---|---|---|---|
| Pro | Leu | Lys | Asp | Met | Gln | Phe | Gly | Asn | Lys | Ile | Ala | Ile | Leu | Ser | Gly | |
| | | | 180 | | | | | 185 | | | | | 190 | | | |

| gac | ttt | ctt | cta | gca | aat | gcc | tgc | aat | gga | cta | gct | ctg | cta | cag | aac | 624 |
|---|---|---|---|---|---|---|---|---|---|---|---|---|---|---|---|---|
| Asp | Phe | Leu | Leu | Ala | Asn | Ala | Cys | Asn | Gly | Leu | Ala | Leu | Leu | Gln | Asn | |
| | | | 195 | | | | | 200 | | | | | 205 | | | |

| acc | aag | gtt | gtg | gaa | ctt | tta | gca | agt | gct | ctt | atg | gac | ttg | gta | caa | 672 |
|---|---|---|---|---|---|---|---|---|---|---|---|---|---|---|---|---|
| Thr | Lys | Val | Val | Glu | Leu | Leu | Ala | Ser | Ala | Leu | Met | Asp | Leu | Val | Gln | |
| | 210 | | | | | 215 | | | | | 220 | | | | | |

| gga | gta | tat | cat | gaa | aat | tct | act | tca | aag | gaa | agt | tat | atc | aca | gat | 720 |
|---|---|---|---|---|---|---|---|---|---|---|---|---|---|---|---|---|
| Gly | Val | Tyr | His | Glu | Asn | Ser | Thr | Ser | Lys | Glu | Ser | Tyr | Ile | Thr | Asp | |
| 225 | | | | | 230 | | | | | 235 | | | | | 240 | |

| gat | att | gga | ata | tcg | act | tgg | aag | gag | cag | act | ttt | ctc | tcc | cat | ggt | 768 |
|---|---|---|---|---|---|---|---|---|---|---|---|---|---|---|---|---|
| Asp | Ile | Gly | Ile | Ser | Thr | Trp | Lys | Glu | Gln | Thr | Phe | Leu | Ser | His | Gly | |
| | | | | 245 | | | | | 250 | | | | | 255 | | |

| gcc | tta | cta | gca | aag | agc | tgc | caa | gct | gca | atg | gaa | tta | gca | aag | cat | 816 |
|---|---|---|---|---|---|---|---|---|---|---|---|---|---|---|---|---|
| Ala | Leu | Leu | Ala | Lys | Ser | Cys | Gln | Ala | Ala | Met | Glu | Leu | Ala | Lys | His | |
| | | | 260 | | | | | 265 | | | | | 270 | | | |

| gat | gct | gag | gtt | cag | aat | atg | gca | ttt | cag | tat | ggg | aag | cac | atg | gcc | 864 |
|---|---|---|---|---|---|---|---|---|---|---|---|---|---|---|---|---|
| Asp | Ala | Glu | Val | Gln | Asn | Met | Ala | Phe | Gln | Tyr | Gly | Lys | His | Met | Ala | |
| | | 275 | | | | | 280 | | | | | 285 | | | | |

| atg | agt | cat | aag | ata | aat | tct | gat | gtc | cag | cct | ttt | att | aaa | gaa | aag | 912 |
|---|---|---|---|---|---|---|---|---|---|---|---|---|---|---|---|---|
| Met | Ser | His | Lys | Ile | Asn | Ser | Asp | Val | Gln | Pro | Phe | Ile | Lys | Glu | Lys | |
| 290 | | | | | 295 | | | | | 300 | | | | | | |

-continued

```
acc agt gac tcc atg act ttt aat cta aac tca gct cct gta gtc tta      960
Thr Ser Asp Ser Met Thr Phe Asn Leu Asn Ser Ala Pro Val Val Leu
305                 310                 315                 320 cat cag gaa ttt ctt gga aga gat ttg tgg att aaa cag atc gga gag     1008
His Gln Glu Phe Leu Gly Arg Asp Leu Trp Ile Lys Gln Ile Gly Glu
                325                 330                 335 gct caa gaa aaa gga aga ttg gac tat gct aag ttg cga gaa aga atc    1056
Ala Gln Glu Lys Gly Arg Leu Asp Tyr Ala Lys Leu Arg Glu Arg Ile
            340                 345                 350 aaa gct ggc aaa ggt gtg act tca gct att gac ctg tgt cgt tac cat    1104
Lys Ala Gly Lys Gly Val Thr Ser Ala Ile Asp Leu Cys Arg Tyr His
355                 360                 365 gga aac aag gca ctg gag gcc ctg gag agc ttt cct ccc tcg gag gcc    1152
Gly Asn Lys Ala Leu Glu Ala Leu Glu Ser Phe Pro Pro Ser Glu Ala
370                 375                 380 aga tct gct tta gaa aac att gtg ttt gct gtg acc aga ttt tca tga   1200
Arg Ser Ala Leu Glu Asn Ile Val Phe Ala Val Thr Arg Phe Ser ***
385                 390                 395
```

<210> SEQ ID NO 4
<211> LENGTH: 399
<212> TYPE: PRT
<213> ORGANISM: human

<400> SEQUENCE: 4

Met Asn Phe Arg Gln Leu Leu Leu His Leu Pro Arg Tyr Leu Gly Ala
 1               5                  10                  15

Ser Gly Ser Pro Arg Arg Leu Trp Trp Ser Pro Ser Leu Asp Thr Ile
             20                  25                  30

Ser Ser Val Gly Ser Trp Arg Gly Arg Ser Ser Lys Ser Pro Ala His
         35                  40                  45

Trp Asn Gln Val Val Ser Glu Ala Glu Lys Ile Val Gly Tyr Pro Thr
     50                  55                  60

Ser Phe Met Ser Leu Arg Cys Leu Leu Ser Asp Glu Leu Ser Asn Ile
 65                  70                  75                  80

Ala Met Gln Val Arg Lys Leu Val Gly Thr Gln His Pro Leu Leu Thr
                 85                  90                  95

Thr Ala Arg Gly Leu Val His Asp Ser Trp Asn Ser Leu Gln Leu Arg
            100                 105                 110

Gly Leu Val Val Leu Leu Ile Ser Lys Ala Ala Gly Pro Ser Ser Val
        115                 120                 125

Asn Thr Ser Cys Gln Asn Tyr Asp Met Val Ser Gly Ile Tyr Ser Cys
    130                 135                 140

Gln Arg Ser Leu Ala Glu Ile Thr Glu Leu Ile His Ile Ala Leu Leu
145                 150                 155                 160

Val His Arg Gly Ile Val Asn Leu Asn Glu Leu Gln Ser Ser Asp Gly
                165                 170                 175

Pro Leu Lys Asp Met Gln Phe Gly Asn Lys Ile Ala Ile Leu Ser Gly
            180                 185                 190

Asp Phe Leu Leu Ala Asn Ala Cys Asn Gly Leu Ala Leu Leu Gln Asn
        195                 200                 205

Thr Lys Val Val Glu Leu Leu Ala Ser Ala Leu Met Asp Leu Val Gln
    210                 215                 220

Gly Val Tyr His Glu Asn Ser Thr Ser Lys Glu Ser Tyr Ile Thr Asp
225                 230                 235                 240

Asp Ile Gly Ile Ser Thr Trp Lys Glu Gln Thr Phe Leu Ser His Gly
                245                 250                 255

```
Ala Leu Leu Ala Lys Ser Cys Gln Ala Met Glu Leu Ala Lys His
        260                 265                 270

Asp Ala Glu Val Gln Asn Met Ala Phe Gln Tyr Gly Lys His Met Ala
        275                 280                 285

Met Ser His Lys Ile Asn Ser Asp Val Gln Pro Phe Ile Lys Glu Lys
        290                 295                 300

Thr Ser Asp Ser Met Thr Phe Asn Leu Asn Ser Ala Pro Val Val Leu
305                 310                 315                 320

His Gln Glu Phe Leu Gly Arg Asp Leu Trp Ile Lys Gln Ile Gly Glu
                325                 330                 335

Ala Gln Glu Lys Gly Arg Leu Asp Tyr Ala Lys Leu Arg Glu Arg Ile
        340                 345                 350

Lys Ala Gly Lys Gly Val Thr Ser Ala Ile Asp Leu Cys Arg Tyr His
        355                 360                 365

Gly Asn Lys Ala Leu Glu Ala Leu Glu Ser Phe Pro Pro Ser Glu Ala
        370                 375                 380

Arg Ser Ala Leu Glu Asn Ile Val Phe Ala Val Thr Arg Phe Ser
385                 390                 395

<210> SEQ ID NO 5
<211> LENGTH: 1206
<212> TYPE: DNA
<213> ORGANISM: mouse

<400> SEQUENCE: 5 atg agc ctc cgg cag ctg ctg ttg cgc ttg tcc ggt tac ctc ggg gct      48
Met Ser Leu Arg Gln Leu Leu Leu Arg Leu Ser Gly Tyr Leu Gly Ala
1               5                   10                  15 tct ggt ccc ccc agt cgc cac tgg tgg tac ttc aga tcc ctc gac agc      96
Ser Gly Pro Pro Ser Arg His Trp Trp Tyr Phe Arg Ser Leu Asp Ser
                20                  25                  30 atc tcc tcg gcg ggc tcc tgg cgc ggg cgc tcc tcc agg tca ccg gcc     144
Ile Ser Ser Ala Gly Ser Trp Arg Gly Arg Ser Ser Arg Ser Pro Ala
            35                  40                  45 cat tgg aac caa gtg gtg tcc gag gcg gag aag atc gtg ggc tac ccc     192
His Trp Asn Gln Val Val Ser Glu Ala Glu Lys Ile Val Gly Tyr Pro
        50                  55                  60 gca tcc ttc atg agc ctg cgc tgc ctg ctg agc gac gag ctc agc aat     240
Ala Ser Phe Met Ser Leu Arg Cys Leu Leu Ser Asp Glu Leu Ser Asn
65                  70                  75                  80 atc gcc atg cag gtg cgg aag ctg gtg ggg acg gga cac cct ctg ctt     288
Ile Ala Met Gln Val Arg Lys Leu Val Gly Thr Gly His Pro Leu Leu
                85                  90                  95 acc act gcc agg gcc ctc gtg cac gac agc cgg cat aac cta caa ctg     336
Thr Thr Ala Arg Ala Leu Val His Asp Ser Arg His Asn Leu Gln Leu
            100                 105                 110 cgg ggc ctg gtc gtg ctc ctc ata tca aag gct gcg ggg ccc agc act     384
Arg Gly Leu Val Val Leu Leu Ile Ser Lys Ala Ala Gly Pro Ser Thr
        115                 120                 125 cgg aac gct tcg tgt cag aac tac gac atg gtc agt ggg gta tac tca     432
Arg Asn Ala Ser Cys Gln Asn Tyr Asp Met Val Ser Gly Val Tyr Ser
    130                 135                 140 tgt caa aga agt ttg gca gag atc aca gaa ctt atc cat act gct ctc     480
Cys Gln Arg Ser Leu Ala Glu Ile Thr Glu Leu Ile His Thr Ala Leu
145                 150                 155                 160 ctg gtg cat cgt ggg ata gta aac tta agt gaa tta cag tca tct gat     528
Leu Val His Arg Gly Ile Val Asn Leu Ser Glu Leu Gln Ser Ser Asp
                165                 170                 175
```

```
gga cca ctg aaa gac atg cag ttt gga aac aaa ata gct atc ctg agt      576
Gly Pro Leu Lys Asp Met Gln Phe Gly Asn Lys Ile Ala Ile Leu Ser
        180                 185                 190 gga gac ttt ctt cta gca aat gca tgc aat gga cta gct ctt cta cag      624
Gly Asp Phe Leu Leu Ala Asn Ala Cys Asn Gly Leu Ala Leu Leu Gln
            195                 200                 205 aac acc aag gtt gtg gag ctt tta tca agt gct ctt atg gac ttg gtg      672
Asn Thr Lys Val Val Glu Leu Leu Ser Ser Ala Leu Met Asp Leu Val
210                 215                 220 cat gga gta tac cag gag aac tct gct tcc acc aag gaa aat tct atc      720
His Gly Val Tyr Gln Glu Asn Ser Ala Ser Thr Lys Glu Asn Ser Ile
225                 230                 235                 240 cca gat gat att gga atc tcg acc tgg aag gag cag act ttc ctg tcc      768
Pro Asp Asp Ile Gly Ile Ser Thr Trp Lys Glu Gln Thr Phe Leu Ser
                245                 250                 255 cat tgt gcc ttg cta gcg aag agc tgc cag gct gca atg gag tta gca      816
His Cys Ala Leu Leu Ala Lys Ser Cys Gln Ala Ala Met Glu Leu Ala
            260                 265                 270 aag cat gat gct gcg gtc caa gac atg gca ttc cag tat ggg aag cac      864
Lys His Asp Ala Ala Val Gln Asp Met Ala Phe Gln Tyr Gly Lys His
        275                 280                 285 atg gcc atg agt cac aag atc aat gct gac ctc cag cct ttt att aaa      912
Met Ala Met Ser His Lys Ile Asn Ala Asp Leu Gln Pro Phe Ile Lys
    290                 295                 300 gac aag gcc agt gac tct aag act ttt aac cta aac tca gca cct gta      960
Asp Lys Ala Ser Asp Ser Lys Thr Phe Asn Leu Asn Ser Ala Pro Val
305                 310                 315                 320 gtc tta cat cag gag ttt ctt gga aga gat ttg tgg att aag cag att     1008
Val Leu His Gln Glu Phe Leu Gly Arg Asp Leu Trp Ile Lys Gln Ile
                325                 330                 335 gga gag gct caa gag aaa gga agc ttg aac tac agt aag ttg cga gaa     1056
Gly Glu Ala Gln Glu Lys Gly Ser Leu Asn Tyr Ser Lys Leu Arg Glu
            340                 345                 350 aca atc aaa gct ggc aaa ggt gtg act tca gct att gac ctg tgt cgt     1104
Thr Ile Lys Ala Gly Lys Gly Val Thr Ser Ala Ile Asp Leu Cys Arg
        355                 360                 365 tac cat gga aac aag gca cta gag gcc ctg gag agc ttc cct ccc tca     1152
Tyr His Gly Asn Lys Ala Leu Glu Ala Leu Glu Ser Phe Pro Pro Ser
    370                 375                 380 gag gcc aga tcg gct tta gaa aac att gtg ttt gct gtg acc aga ttt     1200
Glu Ala Arg Ser Ala Leu Glu Asn Ile Val Phe Ala Val Thr Arg Phe
385                 390                 395                 400 tct tga                                                              1206
Ser

<210> SEQ ID NO 6
<211> LENGTH: 401
<212> TYPE: PRT
<213> ORGANISM: mouse

<400> SEQUENCE: 6

Met Ser Leu Arg Gln Leu Leu Arg Leu Ser Gly Tyr Leu Gly Ala
 1               5                  10                  15

Ser Gly Pro Pro Ser Arg His Trp Trp Tyr Phe Arg Ser Leu Asp Ser
                20                  25                  30

Ile Ser Ser Ala Gly Ser Trp Arg Gly Arg Ser Ser Arg Ser Pro Ala
            35                  40                  45

His Trp Asn Gln Val Val Ser Glu Ala Glu Lys Ile Val Gly Tyr Pro
        50                  55                  60
```

```
Ala Ser Phe Met Ser Leu Arg Cys Leu Leu Ser Asp Glu Leu Ser Asn
 65                  70                  75                  80

Ile Ala Met Gln Val Arg Lys Leu Val Gly Thr Gly His Pro Leu Leu
             85                  90                  95

Thr Thr Ala Arg Ala Leu Val His Asp Ser Arg His Asn Leu Gln Leu
            100                 105                 110

Arg Gly Leu Val Val Leu Leu Ile Ser Lys Ala Ala Gly Pro Ser Thr
            115                 120                 125

Arg Asn Ala Ser Cys Gln Asn Tyr Asp Met Val Ser Gly Val Tyr Ser
130                 135                 140

Cys Gln Arg Ser Leu Ala Glu Ile Thr Glu Leu Ile His Thr Ala Leu
145                 150                 155                 160

Leu Val His Arg Gly Ile Val Asn Leu Ser Glu Leu Gln Ser Ser Asp
                165                 170                 175

Gly Pro Leu Lys Asp Met Gln Phe Gly Asn Lys Ile Ala Ile Leu Ser
            180                 185                 190

Gly Asp Phe Leu Leu Ala Asn Ala Cys Asn Gly Leu Ala Leu Leu Gln
            195                 200                 205

Asn Thr Lys Val Val Glu Leu Leu Ser Ser Ala Leu Met Asp Leu Val
210                 215                 220

His Gly Val Tyr Gln Glu Asn Ser Ala Ser Thr Lys Glu Asn Ser Ile
225                 230                 235                 240

Pro Asp Asp Ile Gly Ile Ser Thr Trp Lys Glu Gln Thr Phe Leu Ser
                245                 250                 255

His Cys Ala Leu Leu Ala Lys Ser Cys Gln Ala Ala Met Glu Leu Ala
            260                 265                 270

Lys His Asp Ala Ala Val Gln Asp Met Ala Phe Gln Tyr Gly Lys His
            275                 280                 285

Met Ala Met Ser His Lys Ile Asn Ala Asp Leu Gln Pro Phe Ile Lys
290                 295                 300

Asp Lys Ala Ser Asp Ser Lys Thr Phe Asn Leu Asn Ser Ala Pro Val
305                 310                 315                 320

Val Leu His Gln Glu Phe Leu Gly Arg Asp Leu Trp Ile Lys Gln Ile
                325                 330                 335

Gly Glu Ala Gln Glu Lys Gly Ser Leu Asn Tyr Ser Lys Leu Arg Glu
            340                 345                 350

Thr Ile Lys Ala Gly Lys Gly Val Thr Ser Ala Ile Asp Leu Cys Arg
            355                 360                 365

Tyr His Gly Asn Lys Ala Leu Glu Ala Leu Glu Ser Phe Pro Pro Ser
370                 375                 380

Glu Ala Arg Ser Ala Leu Glu Asn Ile Val Phe Ala Val Thr Arg Phe
385                 390                 395                 400

Ser

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: primer
      N-dlp1

<400> SEQUENCE: 7
tcgaattcga tgagctttcc gttc                                    24
```

```
<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: primer
      C-dlp1

<400> SEQUENCE: 8
catggatatc gcattc                                                    16

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: primer h
      DLP1-N

<400> SEQUENCE: 9
ctggatccat gaactttcgg cagctgctgt                                     30

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: primer h
      DLP1-C

<400> SEQUENCE: 10
ttcccgggtc atgaaaatct ggtcacagc                                      29

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: primer m
      DLP1-N

<400> SEQUENCE: 11
gcgtcgacga attctatgag cctccggcag                                     30

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: primer m
      DLP1-C

<400> SEQUENCE: 12
ccggatcctc aagaaaatct ggtcacagc                                      29

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: primer
      N-dps

<400> SEQUENCE: 13
tcctgcagca tgattcagta tgta                                           24
```

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: primer C-dps

<400> SEQUENCE: 14
tcgtcgactc acttctttct cgttat     26

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: primer h DPS1-N

<400> SEQUENCE: 15
aagtcgacaa tggcctcgcg ctggtggcgg tg     32

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: primer h DPS1-C

<400> SEQUENCE: 16
ggcggatcct catttatctc ttgtgagtac aatttc     36

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: primer mSDS-N

<400> SEQUENCE: 17
gccatatggc gaattcgatg cgctggtcgt     30

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: primer mSDS-C

<400> SEQUENCE: 18
gcgtcgactc atttatctct ggtg     24

METHOD OF EXPRESSING LONG-CHAIN PRENYL DIPHOSPHATE SYNTHASE

RELATED APPLICATIONS

This application is a nationalization of PCT Application No. PCT/JP02/04566 filed May 10, 2002. This application claims priority from Japanese Patent Application No. 2001-140977 filed on May 11, 2001.

TECHNICAL FIELD

The present invention relates to a protein involved in the expression of a eukaryotes-derived long-chain prenyl diphosphate synthase, a gene coding for such enzyme, a vector containing such enzyme gene, a transformant resulting from transformation with such vector and a long-chain prenyl diphosphate synthase gene-containing expression vector as well as a method of producing a long-chain prenyl diphosphate synthase (in particular decaprenyl diphosphate synthase and solanesyl diphosphate synthase) and of a coenzyme Q having a long-chain isoprenoid in its side chain (in particular coenzyme $Q_9$ or coenzyme $Q_{10}$)

BACKGROUND ART

"Isoprenoids" is a generic name for a variety of compounds, including sterols, carotinoids and terpenes, among others. Among them, there is a group of prenyl diphosphate compounds containing a coenzyme Q side chain, and the synthesis thereof depends on the polymerization-like condensation reaction of isopentenyl diphosphate, which is an isoprene unit containing 5 carbon atoms, as catalyzed by a prenyl diphosphate synthase.

The respective prenyl diphosphate synthases are roughly classified into 4 groups.

The short chain (3 or 4 isoprene units) prenyl diphosphate synthases are known to perform their catalytic function in the form of homodimers. Examples of such are farnesyl diphosphate synthase (Eberthardt, N. L. (1975), J. Biol. Chem., 250, 863-866) and geranylgeranyl diphosphate synthase (Sagami, H. (1994), J. Biol. Chem., 269, 20561-20566).

The medium chain (6 or 7 isoprene units) prenyl diphosphate synthases are known to be heterodimeric enzymes composed of two proteins each independently having no catalytic activity. Examples are hexaprenyl diphosphate synthase (Fujii, H. (1982), J. Biol. Chem., 257, 14610), and heptaprenyl diphosphate synthase (Takahashi, I. (1980), J. Biol. Chem., 255, 4539).

Further, as for the long-chain (8 to 10 isoprene units) prenyl diphosphate synthases, it is reported that prokaryote-derived such enzymes are undissociable homodimers and are activated by a polyprenyl diphosphate carrier protein (Ohnuma, S. (1991), J. Biol. Chem., 266, 23706-23713). At present, however, there is no report available about eukaryotes-derived long-chain prenyl diphosphate synthases.

Coenzymes Q are composed of a quinone skeleton and an isoprenoid side chain and occur widely in a variety of living things, from microorganisms, such as bacteria and yeasts, to higher animals and plants. In prokaryotes, they occur in the plasma membrane and function as electron acceptors for cell membrane stabilization and for periplasmic membrane protein disulfide bond formation. In eukaryotes, they occur in the mitochondrial membrane and/or cytoplasmic membrane, and serve as essential factors in the electron transfer system in the mitochondrial respiratory chain and in the oxidative phosphorylation, function as antioxidants and contribute to the stabilization of biomembranes.

Coenzymes Q having an isoprenoid side chain resulting from condensation of 8 to 10 isoprene units, among others, have attracted attention as materials of health foods and the like. Among them, coenzyme $Q_{10}$ comprising 10 isoprene units is intrinsic in humans and is therefore very useful and is in use as a heart medicine.

Commercially, this coenzyme $Q_{10}$ is produced, for example, by isolating coenzymes Q from a plant, such as tobacco, and synthetically modifying the side chain length thereof.

It is also known that coenzyme $Q_{10}$ is produced by a wide variety of organisms, from microorganisms, such as bacteria and yeasts, to higher animals and plants, and the method comprising cultivating a microorganism and extracting this substance from cells thereof is thought to be one of the most efficient methods of production thereof and, actually, is in use in commercial production thereof. However, such methods cannot be said to be satisfactory in productivity since, for example, the yield is poor and/or the procedure is complicated.

Attempts have also been made to isolate genes involved in biosynthesis of coenzyme $Q_{10}$, amplify the genes by means of the recombinant DNA technology and utilizing them in increasing the production of coenzyme $Q_{10}$. In living organisms, coenzyme $Q_{10}$ is produced via a multistage complicated reaction process in which a number of enzymes are involved. The biosynthetic pathway therefor in prokaryotes differs in part from that in eukaryotes. Basically, however, the pathway comprises three main steps, namely the step of the synthesis of decaprenyl diphosphate to serve as the source of the decaprenyl side chain of coenzyme $Q_{10}$, the step of the synthesis of parahydroxybenzoic acid to serve as the source of the quinone ring, and the step of the coupling of these two compounds, followed by successive substituent conversion to complete coenzyme $Q_{10}$. Among the reactions involved, the reactions involved in decaprenyl diphosphate synthase, which are said to determine the rate of the whole biosynthetic reaction process and which determine the length of the side chain of coenzyme $Q_{10}$, are considered to be the most important reactions.

For efficient production of coenzyme $Q_{10}$, it is considered effective to isolate the decaprenyl diphosphate synthase gene, which is the key gene in the biosynthesis in question, and utilize the same for causing a production increase. Thus, so far, decaprenyl diphosphate synthase genes have been isolated from several microbial species, such as *Schizosaccharomyces pombe* (JP-A-09-173076) and *Gluconobacter suboxydans* (JP-A-10-57072) and studied for their use in coenzyme $Q_{10}$ production. As for the host microorganism for this coenzyme $Q_{10}$ production, it is desirable to use prokaryotes, such as *Escherichia coli*, from the viewpoint of productivity, safety, recombinant system preparation, and so on.

As for the decaprenyl diphosphate synthase gene sources, it is also possible to utilize eukaryotes in which coenzyme $Q_{10}$ is produced in relatively large amounts. Thus, for example, fungi are strong candidates. However, when a eukaryote-derived decaprenyl diphosphate synthase gene was introduced by recombination into those microorganisms which belong to the prokaryotes, for example *Escherichia coli*, coenzyme $Q_{10}$ was not produced or was produced only in unsatisfactory amounts. It is thought that this is due to an insufficient level of expression of the long-chain prenyl diphosphate synthase. Therefore, the development of a method of causing efficient expression, in prokaryotes, of a eukaryote-derived decaprenyl diphosphate synthase gene serving in relatively abundant coenzyme Q10 production has been desired.

SUMMARY OF THE INVENTION

It is an object of the present invention to provide a protein involved in the expression of a eukaryotes-derived long-chain prenyl diphosphate synthase, a gene coding for such enzyme, a vector containing such enzyme gene, a transformant resulting from transformation with such vector and a long-chain prenyl diphosphate synthase gene-containing expression vector as well as a method of producing a long-chain prenyl diphosphate synthase (in particular decaprenyl diphosphate synthase and solanesyl diphosphate synthase) and of a coenzyme Q having a long-chain isoprenoid in its side chain (in particular coenzyme $Q_9$ or coenzyme $Q_{10}$).

Presupposing that, in the group of long-chain prenyl diphosphate synthase-biosynthesizing eukaryotes, there might be two forms of prenyl diphosphate synthase, the present inventors considered that when derived from the genus *Saitoella* or the like, the enzyme of which recombinant gene expression in *Escherichia coli*, a prokaryote, had been confirmed would be expressed in the homo form and that when derived from the genus *Schizosaccharomyces* or the like, the enzyme of which recombinant gene expression in *Escherichia coli* could not be confirmed would be expressed in the hetero form. Thus, they considered that there might be another gene involved in the expression of such a long-chain prenyl diphosphate synthase gene incapable of being expressed upon gene recombination and the long-chain prenyl diphosphate synthase gene would be expressed with the cooperation of the other gene and that, therefore, transformation of a prokaryotic host, such as *Escherichia coli*, with the long-chain prenyl diphosphate synthase gene alone could not result in satisfactory activity production.

Accordingly, they made investigations in an attempt to isolate a gene involved in the activity expression of a eukaryote-derived long-chain prenyl diphosphate synthase gene and succeeded in isolating genes enhancing the expression, in *Escherichia coli*, of the eukaryote-derived long-chain prenyl diphosphate synthase gene from a microorganism belonging to the genus *Schizosaccharomyces* and the higher animals mouse and human. Thus, they have now completed the present invention.

The present invention thus relates to a DNA defined below under (a), (b) or (c):
(a) a DNA having a base sequence shown under SEQ ID NO:1, 3 or 5 and coding for a protein enabling or enhancing the activity expression of a eukaryote-derived long-chain prenyl diphosphate synthase in a host microorganism;
(b) a DNA having a base sequence derived from the base sequence shown under SEQ ID NO:1, 3 or 5 by deletion, addition, insertion and/or substitution of one to several bases thereof and coding for a protein enabling or enhancing the activity expression of a eukaryote-derived long-chain prenyl diphosphate synthase in a host microorganism;
(c) a DNA capable of hybridizing with a DNA comprising the base sequence shown under SEQ ID NO:1, 3 or 5 under a stringent condition and coding for a protein enabling or enhancing the activity expression of a eukaryote-derived long-chain prenyl diphosphate synthase in a host microorganism.

The invention also relates to a protein defined below under (d) or (e):
(d) a protein having an amino acid sequence shown under SEQ ID NO:2, 4 or 6 and enabling or enhancing the activity expression of a eukaryote-derived long-chain prenyl diphosphate synthase in a host microorganism;
(e) a protein having an amino acid sequence derived from the amino acid sequence shown under SEQ ID NO:2, 4 or 6 by deletion, addition, insertion and/or substitution of one to several amino acid residues and enabling or enhancing the activity expression of a eukaryote-derived long-chain prenyl diphosphate synthase in a host microorganism.

The invention further relates to a DNA coding for the protein defined above under (d) or (e).

Further, the invention relates to an expression vector resulting from insertion of the above DNA into a vector for expression; the expression vector as defined above wherein the vector for expression is pSTV28; the expression vector as defined above which is pSTVDLP1; the expression vector as defined above which is pSTVK28-mDLP1; and the expression vector as defined above which is pSTVK28-hDLP1.

Furthermore, the invention relates to a transformant resulting from transformation of a host microorganism with the above DNA; a transformant resulting from transformation of a host microorganism with the above expression vector; the transformant as defined above wherein the host microorganism is *Escherichia coli*; the transformant as defined above which is *E. coli* DH5α(pSTVDLP1) (FERM BP-7433); the transformant as defined above which is *E. coli* DH5α (pSTVK28-mDLP1); and the transformant as defined above which is *E. coli* DH5α(pSTVK28-hDLP1).

The invention further relates to the transformant as defined above which harbors a eukaryote-derived long-chain prenyl diphosphate synthase gene further introduced therein; the transformant as defined above wherein the eukaryote-derived prenyl diphosphate synthase gene is a gene derived from a microorganism belong to the genus *Schizosaccharomyces*, *Saitoella*, *Rhodotorula*, *Leucosporidium*, *Aspergillus* or *Bulleomryces*, a human-derived gene or a mouse-derived gene; the transformant as defined above which is *E. coli* DH5α (pSTVDLP1, pBSDPS) (FERM BP-7548); the transformant as defined above which is *E. coli* DH5α(pSTVDLP1, pUhDPS1) (FERM BP-8025); the transformant as defined above which is *E. coli* DH5α(pSTVDLP1, pBmSDS1); the transformant as defined above which is *E. coli* DH5α(pSTVK28-mDLP1, pUhDPS1); the transformant as defined above which is *E. coli* DH5α(pSTVK28-mDLP1, pBmSDS1) (FERM BP-8027); the transformant as defined above which is *E. coli* DH5α(pSTVK28-hDLP1, pUhDPS1) (FERM BP-8026); or the transformant as defined above which is *E. coli* DH5α(pSTVK28-hDLP1, pBmSDS1).

Still further, the invention relates to a method of producing coenzymes Q which comprises cultivating the transformant as defined above in a medium to cause formation and accumulation of a coenzyme Q in the culture and recovering the same.

DETAILED DISCLOSURE OF THE INVENTION

In the following, the present invention is described in detail.

The DNAs of the invention were isolated as follows.

Using the sequence of the decaprenyl diphosphate synthase gene of the genus *Schizosaccharomyces*, a homology search was conducted from a chromosomal database for the genus *Schizosaccharomyces*, and gene relatively high in homology was found out. Based on the above-mentioned gene sequence, genes relatively high in homology were also found out from chromosomal databases for the mouse and human, respectively.

For separating the thus-found gene from the chromosome of the genus *Schizosaccharomyces*, PCR primers, N-dlp1 (SEQ ID NO:7) and C-dlp1 (SEQ ID NO:8) were synthesized. For the separation from the human chromosome, hDLP1-N (SEQ ID NO: 9) and hDLP1-C (SEQ ID NO:10) were synthesized and, for the separation from the murine chromosome, mDLP1-N (SEQ ID NO:11) and mDLP1-C (SEQ ID NO:12) were synthesized.

Using these primers, the PCR conditions were studied and determined, and PCR was carried out by 2 minutes of heat treatment at 94° C. and 25 repetitions of the cycle one minute at 94° C.→one minute at 56° C.→two minutes at 72° C. That a DNA of about 900 bp was amplified from the chromosomal gene of *Schizosaccharomyces pombe* IFO 1628, a DNA about 1,200 bp from the human chromosome, and a DNA about 1,200 bp from the murine chromosome was revealed by analyzing the base sequences of the respective genes. The DNAs obtained were sequenced and found to have the base sequences shown in the sequence listing under SEQ ID NO:1, 3, and 5, respectively.

The DNA of the present invention, which is a DNA coding for a protein enabling or enhancing the activity expression of a eukaryote-derived long-chain prenyl diphosphate synthase in a host microorganism, may be a DNA having the base sequence shown under SEQ ID NO:1, 3 or 5, or a DNA having a base sequence derived from the base sequence shown under SEQ ID NO:1, 3 or 5 by deletion, addition, insertion and/or substitution of one to several bases, or a DNA capable of hybridizing with the DNA comprising the base sequence shown under SEQ ID NO:1, 3 or 5 under a stringent condition.

Since a number of amino acids are encoded by one or more codons (genetic code degeneracy), not only the DNA comprising the base sequence shown under SEQ ID NO:1, 3 or 5 but also a number of other DNAs code for a protein comprising the amino acid sequence shown under SEQ ID NO:2, 4 or 6. Therefore, the DNA of the invention includes those DNAs coding for a protein comprising the amino acid sequence shown under SEQ ID NO:2, 4 or 6.

The term "base sequence derived from a base sequence by deletion, addition, insertion and/or substitution of one to several bases" as used herein means a base sequence resulting from deletion, addition, insertion and/or substitution of such a number of bases as can be deleted, added, inserted and/or substituted by a method well known to those skilled in the art as described in Supplemental Issue, Tanpakushitsu, Kakusan, Koso (Protein, Nucleic Acid and Enzyme), PCR Method for Gene Amplification, TAKKAJ, 35 (17), 2951-3178 (1990) or Henry A. Erlich (ed.), translated into Japanese under the supervision of Ikunoshin Kato: PCR Technology (1990), for instance.

The term "DNA capable of hybridizing with a DNA comprising the base sequence shown under SEQ ID NO:1, 3 or 5 under a stringent condition" means a DNA obtained by the colony hybridization, plaque hybridization or Southern hybridization technique, among others, using, as a probe, the DNA comprising the base sequence shown under SEQ ID NO:1, 3 or 5. Those skilled in the art can easily obtain any desired DNA by conducting such hybridization according to the method described in Molecular Cloning, 2nd Edt. (Cold Spring Harbor Laboratory Press, 1989). For example, the desired DNA can be obtained by carrying out the hybridization at a temperature of not lower than 50° C. in urea-free SSC having a salt concentration of not higher than 0.5 M.

Further, the term "protein enabling or enhancing the activity expression of a eukaryote-derived long-chain prenyl diphosphate synthase in a host microorganism" indicates a protein that increases the coenzyme Q production in the host microorganism by causing a eukaryote-derived long-chain prenyl diphosphate synthase gene to be expressed in the host microorganism harboring the gene as introduced therein and thus enabling or enhancing the expression of the long-chain prenyl diphosphate synthase activity.

Whether a protein is such a protein or not can be checked by preparing a transformant resulting from transformation with the long-chain prenyl diphosphate synthase gene alone and a transformant resulting from transformation with the long-chain prenyl diphosphate synthase gene together with a DNA coding for the protein in question and measuring and comparing the coenzyme Q productions in both transformants under the same conditions. In other words, when the coenzyme Q production is absolutely zero or little in the transformant resulting from transformation with the long-chain prenyl diphosphate synthase gene alone but the coenzyme Q production is significant in the transformant resulting from transformation with the long-chain prenyl diphosphate synthase gene together with the DNA coding for the protein in question, the protein corresponds to the one defined hereinabove.

The protein of the invention, which is a protein enabling or enhancing (potentiating) the activity expression of a eukaryote-derived long-chain prenyl diphosphate synthase in a host microorganism, may be a protein having the amino acid sequence shown under SEQ ID NO:2, 4, or 6, or a protein having an amino acid sequence derived from the amino acid sequence shown under SEQ ID NO:2, 4 or 6 by deletion, addition, insertion and/or substitution of one to several amino acid residues.

The "amino acid sequence derived by deletion, addition, insertion and/or substitution of one to several amino acid residues" so referred to herein can be obtained by deleting, adding, inserting and/or substituting such a number of amino acid residues as can be deleted, added, inserted and/or substituted by a method well known to those skilled in the art, for example by the technique of site-specific mutagenesis. Such method is more specifically described in the literature, for example Nucleic Acids Res., 10, 6487 (1982), and Methods in Enzymology, 100, 448 (1983).

For causing the protein of the invention to be expressed, it is necessary to join the gene for the protein to the downstream of an appropriate promoter. For example, an expression vector can be prepared by excising a DNA fragment containing the gene with restriction enzyme treatment, or amplifying, by PCR, the enzyme-encoding gene segment alone, and inserting this into a promoter-containing vector for expression.

The expression vector of the invention comprises a vector for expression with the above-mentioned DNA inserted therein.

The vector for expression is not particularly restricted but may be, for example, one resulting from insertion of an appropriate promoter into an *Escherichia coli*-derived plasmid. As the *Escherichia coli*-derived plasmid, there may be mentioned, for example, pSTV28, pBR322, pBR325, pUC19, and pUC119. As the promoter, there may be mentioned, for example, the T7 promoter, trp promoter, tac promoter, lac promoter, and APL promoter.

In the practice of the invention, pGEX-2T, pGEX-3T, pGEX-3X (the three being products of Pharmacia), pBluescript II, pUC19 (product of Toyobo), pMALC2, pET-3T, pUCNT (described in WO 94/03613) and the like may also be used as the vector for expression.

Among them, pSTV28 is suitably used. In specific examples, an expression vector designated as pSTVDLP1 can be constructed by inserting a DNA comprising the base sequence shown under SEQ ID NO:1 into the vector pSTV28 for expression, an expression vector designated as pSTVK28-hDLP1 by inserting a DNA comprising the base sequence shown under SE ID NO:3 into pSTV28, and an expression vector designated as pSTVK28-mDLP1 by inserting a DNA comprising the base sequence shown under SEQ ID NO:5 into pSTV28.

The transformant of the invention may be one resulting from transformation of a host microorganism with the DNA mentioned above, or one resulting from transformation of a host microorganism with the expression vector mentioned above, or one resulting from transformation of a host microorganism with the above-mentioned DNA or expression vector together with a eukaryote-derived long-chain prenyl diphosphate synthase gene used additionally.

By introducing the above expression vector, together with an expression vector containing a eukaryote-derived long-chain prenyl diphosphate synthase gene, into an appropriate host microorganism, it becomes possible to utilize the resulting transformant in coenzyme Q production.

The eukaryote to serve as the long-chain prenyl diphosphate synthase gene source is not particularly restricted but includes, among others, decaprenyl diphosphate synthase-producing microorganisms belonging to the genera *Schizosaccharomyces*, *Saitoella*, *Rhodotorula*, *Leucosporidium*, *Aspergillus*, *Bulleomyces* and the like, human beings, and solanesyl diphosphate synthase-producing mice.

The host microorganism is not particularly restricted. *Escherichia coli* and the like are suitably used, however. The species of *Escherichia coli* is not particularly restricted but includes XL1-Blue, BL-21, JM109, NM522, DH5α, HB101, and DH5, among others. Among them, *Escherichia coli* DH5α is suitably used.

When, for example, the above-mentioned expression vector pSTVDLP1 is introduced, together with an expression vector for the decaprenyl diphosphate synthase gene derived from the genus *Schizosaccharomyces*, into *Escherichia coli*, the microorganism can be converted into a transformant capable of producing significant amounts of coenzyme $Q_{10}$ which originally cannot be produced in *Escherichia coli*.

The transformant of the invention includes, among others, the following:

The *E. coli* strain DH5α(pSTVDLP1) resulting from transformation with pSTVDLP1;

The *E. coli* strain DH5α(pSTVK28-mDLP1) resulting from transformation with pSTVK28-mDLP1;

The *E. coli* strain DH5α(pSTVK28-hDLP1) resulting from transformation with pSTVK28-hDLP1;

The *E. coli* strain DH5α(pSTVDLP1, pBSDPS) resulting from transformation with pSTVDLP1 and pBSDPS;

The *E. coli* strain DH5α(pSTVDLP1, pUhDPS1) resulting from transformation with pSTVDLP1 and pUhDPS1;

The *E. coli* strain DH5α(pSTVDLP1, pBmSDS1) resulting from transformation with pSTVDLP1 and pBmSDS1;

The *E. coli* strain DH5α(pSTVK28-mDLP1, pUhDPS1) resulting from transformation with pSTVK28-mDLP1 and pUhDPS1;

The *E. coli* strain DH5α(pSTVK28-mDLP1, pBmSDS1) resulting from transformation with pSTVK28-mDLP1 and pBmSDS1;

The *E. coli* strain DH5α(pSTVK28-hDLP1, pUhDPS1) resulting from transformation with pSTVK28-hDLP1 and pUhDPS1; and The *E. coli* strain DH5α(pSTVK28-hDLP1, pBmSDS1) resulting from transformation with pSTVK28-hDLP1 and pBmSDS1.

Among them, *E. coli* DH5α(pSTVDLP1) has been deposited with the National Institute of Advanced Industrial Science and Technology International Patent Organism Depositary, Central 6, 1-1-1 Higashi, Tsukuba, Ibaraki, Japan as of Jan. 18, 2001 under the accession number FERM BP-7433,

*E. coli* DH5α(pSTVDLP1, pBSDPS) as of Apr. 17, 2001 under the accession number FERM BP-7548,

*E. coli* DH5(pSTVDLP1, pUhDPS1) as of Apr. 19, 2002 under the accession number FERM BP-8025,

*E. coli* DH5α(pSTVK28-mDLP1, pBmSDS1) as of Apr. 19, 2002 under the accession number FERM BP-8027, and

*E. coli* DH5α(pSTVK28-hDLP1, pUhDPS1) as of Apr. 19, 2002 under the accession number FERM BP-8026.

By using the DNA of the invention combinedly with a eukaryote-derived long-chain prenyl diphosphate synthase gene expression vector and, in addition, introducing another gene involved in the biosynthesis of a coenzyme Q simultaneously into the microorganism employed, it becomes possible to expect a still better result.

As the other gene, there may be mentioned, for example, the polyprenyl diphosphate transferase gene and the like.

A coenzyme Q can be produced in the conventional manner by cultivating the transformant obtained in accordance with the invention in a medium and recovering the coenzyme Q form the culture.

In cases where the host microorganism is *Escherichia coli*, LB medium, M9 medium containing glucose and/or casamino acids, and the like can be used as the medium. For efficient promoter functioning, such an agent as isopropylthiogalactoside and/or indolyl-3-acrylic acid, for instance, maybe added to the medium. The cultivation is carried out, for example, at 20 to 40° C., preferably at 30 to 37° C., more preferably at 37° C., for 17 to 24 hours and, on that occasion, aeration, agitation and the like may be made according to need.

In the practice of the invention, the coenzyme Q obtained may be optionally purified or used in the form of a roughly purified product according to the intended use thereof.

For coenzyme Q purification from the culture obtained, an appropriate combination of separation/purification methods known in the art can be used. As the separation/purification methods known in the art, there may be mentioned the methods utilizing the difference in electric charge, such as ion exchange chromatography, the methods utilizing the difference in specific affinity, such as affinity chromatography, and the methods utilizing the difference in hydrophobicity, such as reversed phase high-performance liquid chromatography, among others.

The use of the coenzyme Q obtained in accordance with the invention is not particularly restricted but the coenzyme Q can be suitably used in drugs, foods and so forth.

BEST MODES FOR CARRYING OUT THE INVENTION

The following examples illustrate the present invention in further detail. These examples are, however, by no means limitative of the scope of the invention.

EXAMPLE 1

Using the base sequence of the decaprenyl diphosphate synthase gene of *Schizosaccharomyces pombe*, homology search was conducted in the Sanger Center database and, as a result, a gene having 26% homology was found out by means of GENETYX (Software Development Co., Ltd.). PCR primers, N-dlp1 (SEQ ID NO:7) and C-dlp1 (SEQ ID NO:8), were prepared for obtaining that gene. Separately, the chromosomal DNA of *Schizosaccharomyces pombe* IFO 1628 was prepared by the method of C. S. Hoffman et al. (Gene, 57 (1987), 267-272). Using these, PCR was carried out by 2 minutes of heat treatment at 94° C. followed by 25 repetitions of the following cycle: one minute at 94° C.→one minute at 56° C.→two minutes at 72° C. The thus-amplified DNA was analyzed by 0.7% agarose gel electrophoresis.

Figure 1:
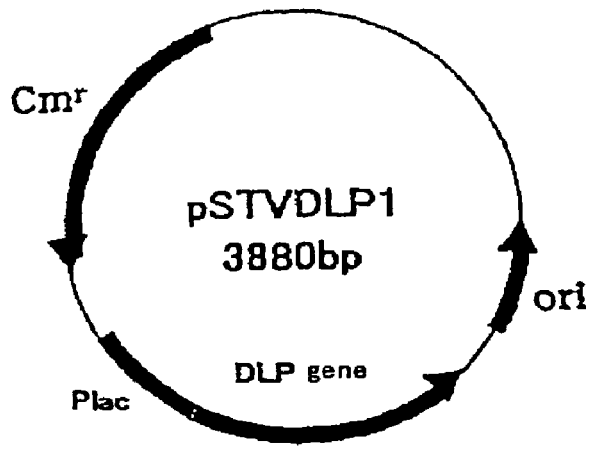
FIG. 1 is a restriction enzyme map of the expression vector pSTVDLP1.

The thus-obtained fragment of about 900 bp was excised from the gel, purified using a DNA extraction kit (Sephaglas (trademark) BandPrep Kit, product of Amersham Pharmacia Biotech) and then cloned in a vector for expression in *Escherichia coli* using a PCR product direct cloning kit (pT7BlueT-Vector Kit, product of NOVAGEN) to give pT7-DLP1. The DNA base sequence was determined using a DNA sequencer (model 377, product of Perkin Elmer) and a DNA sequencing kit (product of Perkin Elmer, ABI PRISM (trademark) BigDye (trademark) Terminator Cycle Sequence Ready Reaction Kit with AmpliTaq (registered trademark) DNA polymerase, FS) and conducting the reactions according to the manual attached to the kit. As a result, the full-length sequence occurring on the database could be obtained.

pT7-DLP1 was cleaved with the restriction enzymes EcoRI and EcoRV (products of Takara Shuzo), followed by 0.8% agarose gel electrophoresis. The fragment of about 900 bp was excised from the gel and purified using a DNA extraction kit (Sephaglas (trademark) BandPrep Kit, product of Amersham Pharmacia Biotech), and this DNA fragment was then inserted into pSTV28 (product of Takara Shuzo) at the EcoRI-SmaI site. The DNA base sequence was determined using a DNA sequencer (model 377, product of Perkin Elmer) and a DNA sequencing kit (product of Perkin Elmer, ABI PRISM (trademark) BigDye (trademark) Terminator Cycle Sequence Ready Reaction Kit with AmpliTaq (registered trademark) DNA polymerase, FS) and conducting the reactions according to the manual attached to the kit. As a result, an expression vector, pSTVDLP1, could be obtained. A restriction enzyme map of the expression vector pSTVDLP1 is shown in FIG. 1.

The *E. coli* DH5α(pSTVDLP1) strain obtained by transformation with the above-obtained pSTVDLP1 has been deposited with the National Institute of Advanced Industrial Science and Technology International Patent Organism Depositary, Central 6, 1-1-1 Higashi, Tsukuba, Ibaraki, Japan as of Jan. 18, 2001 under the accession number FERM BP-7433.

EXAMPLE 2

Using the base sequence of the DLP1 gene of *Schizosaccharomyces pombe* as obtained in Example 1, homology search was conducted in a Genbank database and, as a result, a gene having 27% homology was found out by means of GENETYX (Software Development Co., Ltd.). PCR primers, hDLP1-N (SEQ ID NO:9) and hDLP1-C (SEQ ID NO:10), were prepared for obtaining that gene. Using a human liver cDNA library (cDNA Library, Human Liver, plasmid type (product of Takara Shuzo)) as a template, PCR was carried out by 2 minutes of heat treatment at 94° C. followed by 35 repetitions of the following cycle: one minute at 94° C.→one minute at 56° C.→two minutes at 72° C. The thus-amplified DNA was analyzed by 0.7% agarose gel electrophoresis.

Figure 2:
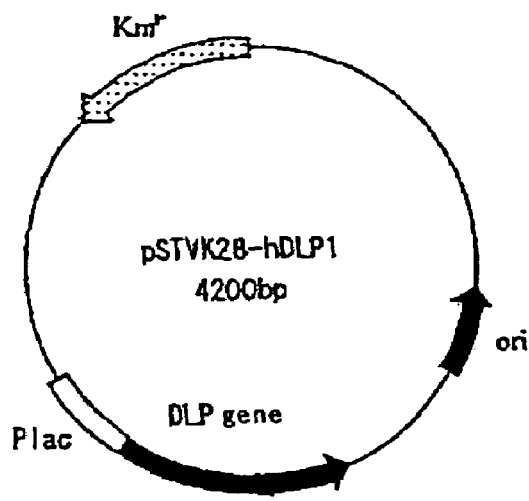
FIG. 2 is a restriction enzyme map of the expression vector pSTVK28-hDLP1.

The thus-obtained fragment of about 1,200 bp was excised from the gel, purified using a DNA extraction kit (Sephaglas (trademark) BandPrep Kit, product of Amersham Pharmacia Biotech) and then cloned in a vector for expression in *Escherichia coli* using a PCR product direct cloning kit (pT7BlueT-Vector Kit, product of NOVAGEN) to give pT7-hDLP1. The DNA base sequence was determined using a DNA sequencer (model 377, product of Perkin Elmer) and a DNA sequencing kit (product of Perkin Elmer, ABI PRISM (trademark) BigDye (trademark) Terminator Cycle Sequence Ready Reaction Kit with AmpliTaq (registered trademark) DNA polymerase, FS) and conducting the reactions according to the manual attached to the kit. As a result, the full-length sequence occurring on the database could be obtained.

pT7-hDLP1 was cleaved with the restriction enzymes BamHI and HindIII (products of Takara Shuzo), followed by 0.8% agarose gel electrophoresis. The fragment of about 1,200 bp was excised from the gel and purified using a DNA extraction kit (Sephaglas (trademark) BandPrep Kit, product of Amersham Pharmacia Biotech), and this DNA fragment was then inserted into pSTV28 (product of Takara Shuzo) at the BamHI-HindIII site. The DNA base sequence was determined using a DNA sequencer (model 377, product of Perkin Elmer) and a DNA sequencing kit (product of Perkin Elmer, ABI PRISM (trademark) BigDye (trademark) Terminator Cycle Sequence Ready Reaction Kit with AmpliTaq (registered trademark) DNA polymerase, FS) and conducting the reactions according to the manual attached to the kit. As a result, an expression vector, pSTVK28-hDLP1, could be obtained. A restriction enzyme map of the expression vector pSTVK28-hDLP1 is shown in FIG. 2. An *Escherichia coli* strain, DH5α(pSTVK28-hDLP1), was obtained by transformation with pSTVK28-hDLP1.

EXAMPLE 3

Using the base sequence of the DLP1 gene of *Schizosaccharomyces pombe* as obtained in Example 1, homology search was conducted in a Genbank database and, as a result, a gene having 31% homology was found out by means of GENETYX (Software Development Co., Ltd.). PCR primers, mDLP1-N (SEQ ID NO:11) and mDLP1-C (SEQ ID NO:12), were prepared for obtaining that gene. Using a murine liver cDNA library (cDNA Library, Mouse Liver, plasmid type (product of Takara Shuzo)) as a template, PCR was carried out by 2 minutes of heat treatment at 94° C. followed by 35 repetitions of the following cycle: one minute at 94° C.→one minute at 56° C.→two minutes at 72° C. The thus-amplified DNA was analyzed by 0.7% agarose gel electrophoresis.

Figure 3:
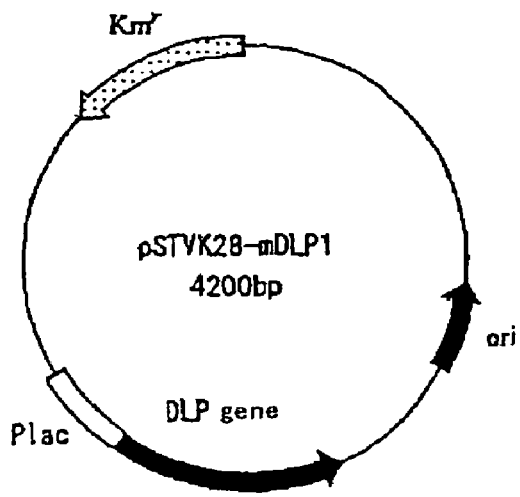
FIG. 3 is a restriction enzyme map of the expression vector pSTVK28-mDLP1.
Figure 4:
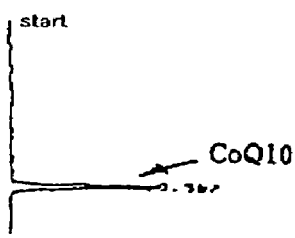
FIG. 4 to FIG. 8 show HPLC analysis charts for the products formed by a host and transformants thereof.
Figure 4:
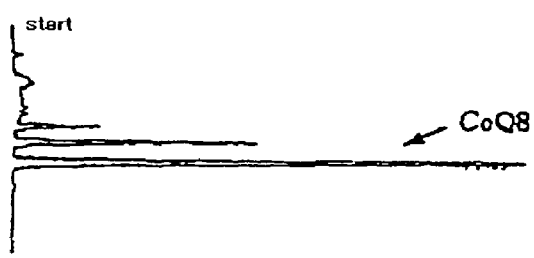
Figure 4:
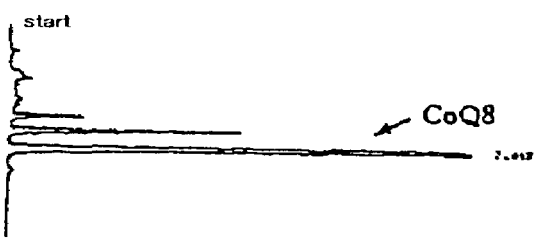
Figure 4:
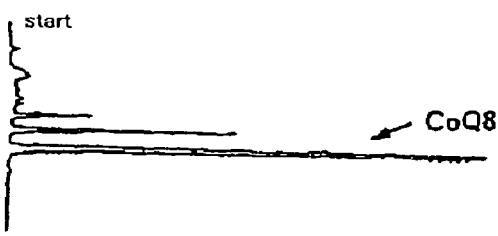
Figure 4:
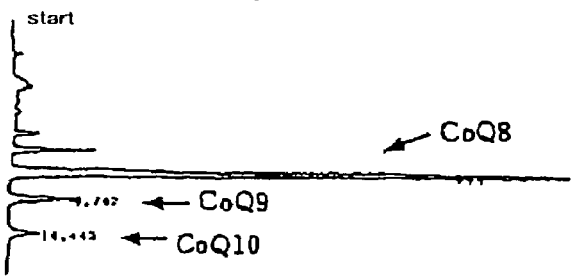
Figure 5:
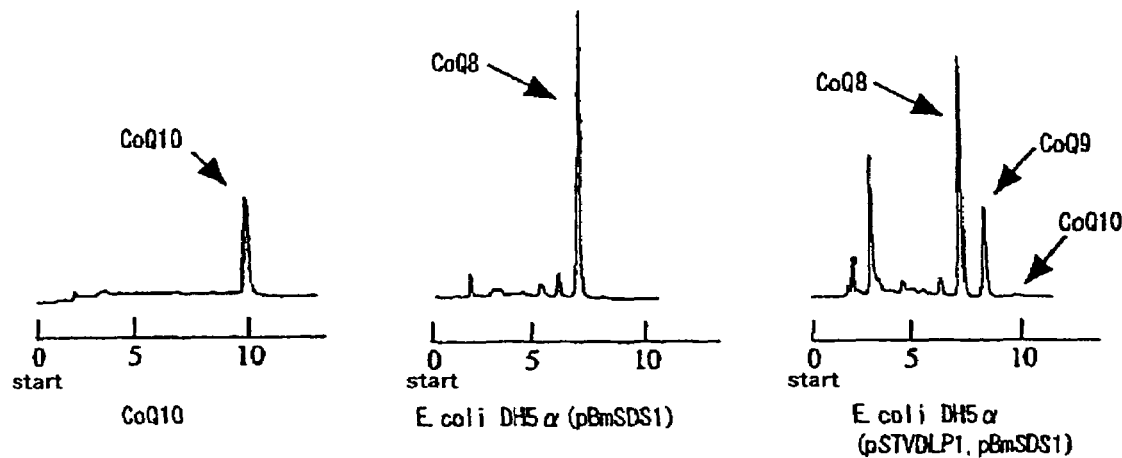
Figure 6:
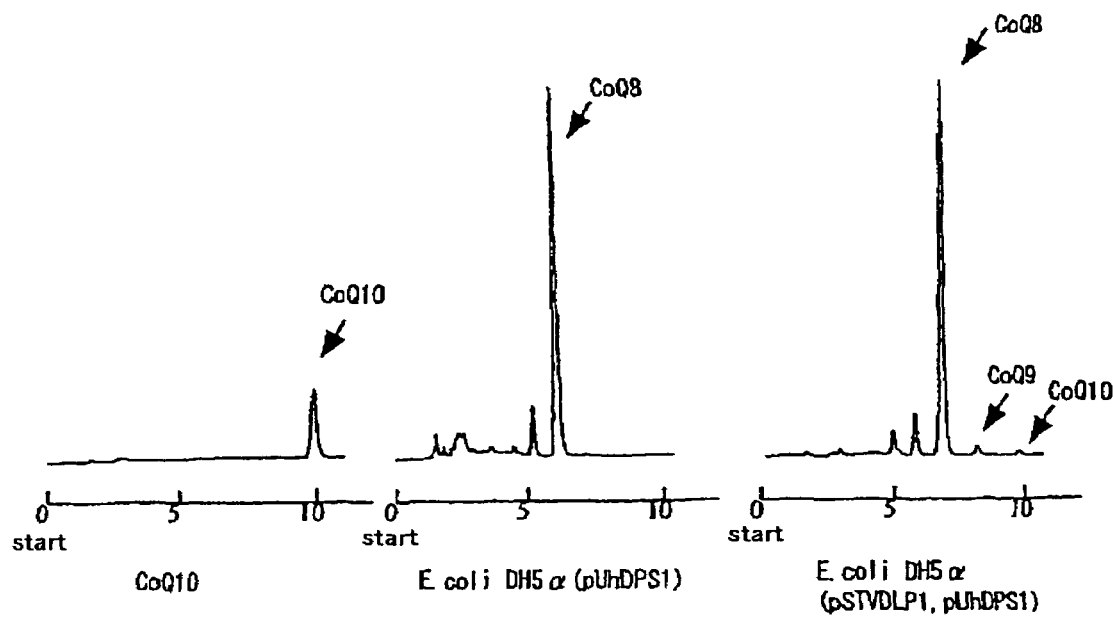
Figure 7:
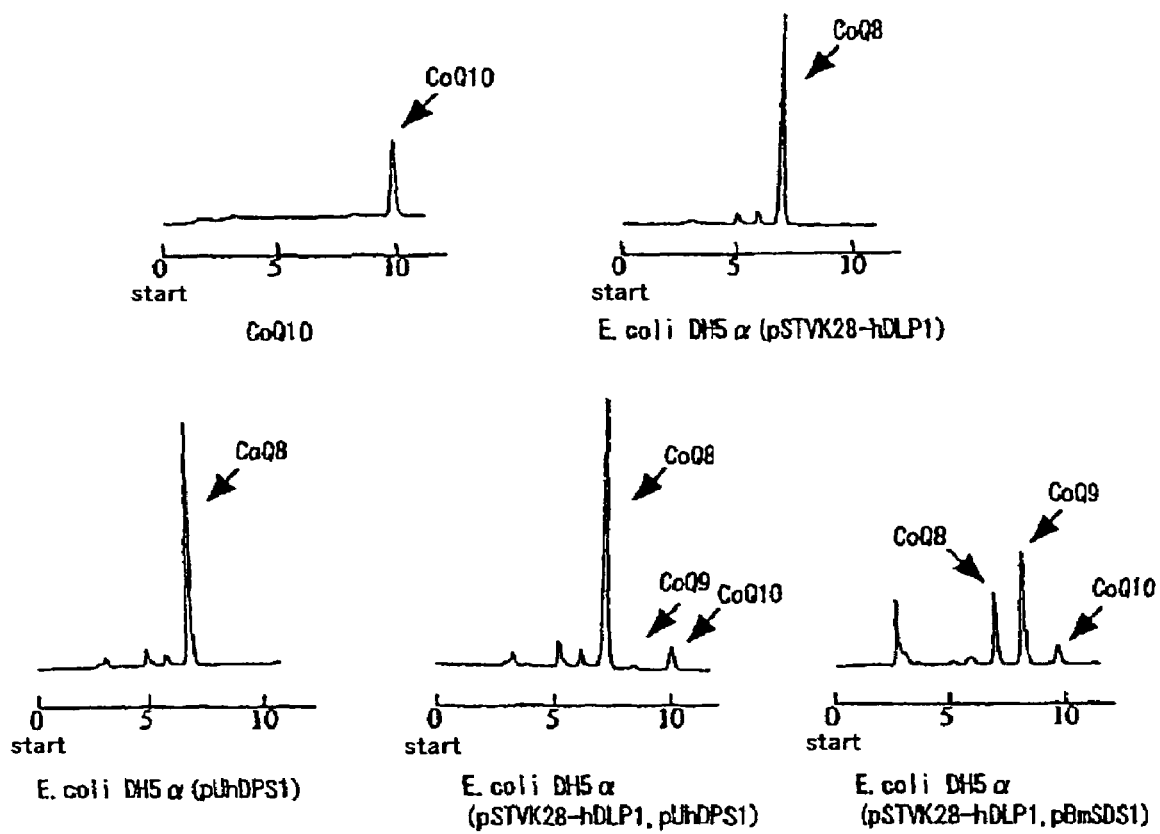
Figure 8:
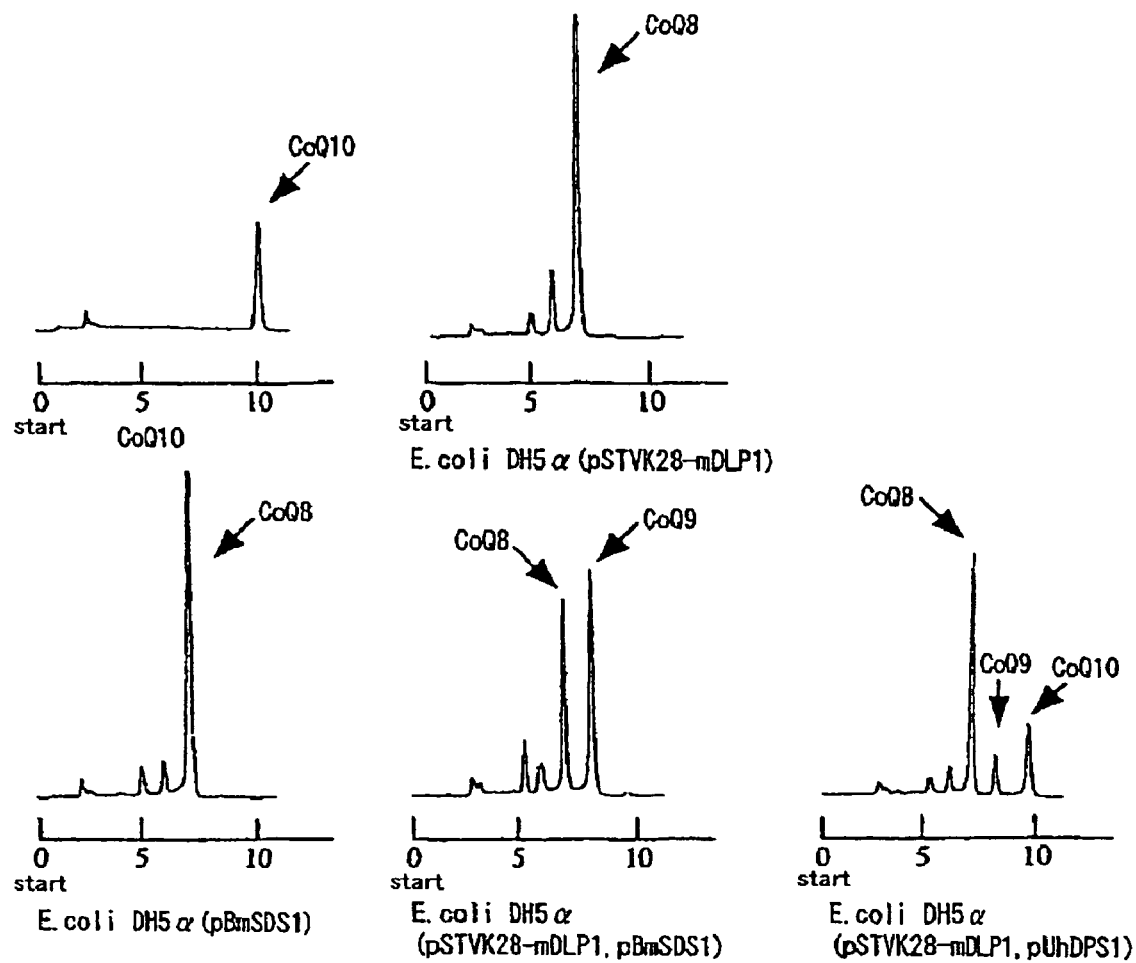

The thus-obtained fragment of about 1,200 bp was excised from the gel, purified using a DNA extraction kit (Sephaglas (trademark) BandPrep Kit, product of Amersham Pharmacia Biotech) and then cloned in a vector for expression in *Escherichia coli* using a PCR product direct cloning kit (pT7BlueT-Vector Kit, product of NOVAGEN) to give pT7-mDLP1. The DNA base sequence was determined using a DNA sequencer (model 377, product of Perkin Elmer) and a DNA sequencing kit (product of Perkin Elmer, ABI PRISM (trademark) BigDye (trademark) Terminator Cycle Sequence Ready Reaction Kit with AmpliTaq (registered trademark) DNA polymerase, FS) and conducting the reactions according to the manual attached to the kit. As a result, the full-length sequence occurring on the database could be obtained.

pT7-mDLP1 was cleaved with the restriction enzymes EcoRI and BamHI (products of Takara Shuzo), followed by 0.8% agarose gel electrophoresis. The fragment of about 1,200 bp was excised from the gel and purified using a DNA extraction kit (Sephaglas (trademark) BandPrep Kit, product of Amersham Pharmacia Biotech), and this DNA fragment was then inserted into pSTV28 (product of Takara Shuzo) at the EcoRI-BamHI site. The DNA base sequence was determined using a DNA sequencer (model 377, product of Perkin Elmer) and a DNA sequencing kit (product of Perkin Elmer, ABI PRISM (trademark) BigDye (trademark) Terminator Cycle Sequence Ready Reaction Kit with AmpliTaq (registered trademark) DNA polymerase, FS) and conducting the reactions according to the manual attached to the kit. As a result, an expression vector, pSTVK28-mDLP1, could be obtained. A restriction enzyme map of the expression vector pSTVK28-mDLP1 is shown in FIG. 3. An *Escherichia coli* strain, DH5α(pSTVK28-mDLP1), was obtained by transformation with pSTVK28-mDLP1.

EXAMPLE 4

Using pKS18 (Suzuki, K., J. Biochem., 121, 496-505 (1997)) having a *Schizosaccharomyces pombe* cDNA-derived decaprenyl diphosphate synthase gene and primers, N-dps (SEQ ID NO:13) and C-dps (SEQ ID NO:14), PCR was carried out by 2 minutes of heat treatment at 94° C. followed by 25 repetitions of the following cycle: one minute at 94° C.→one minute at 56° C.→two minutes at 72° C. The thus-amplified DNA was analyzed by 0.7% agarose gel electrophoresis.

The thus-obtained fragment of about 1,100 bp was excised from the gel, purified using a DNA extraction kit (Sephaglas (trademark) BandPrep Kit, product of Amersham Pharmacia Biotech) and then inserted into the vector pBluescript II for expression in *Escherichia coli* at the SalI-PstI site to give an expression vector, pBSDPS. *Escherichia coli* DH5α was transformed with this vector to give *E. coli* DH5α(pBSDPS).

This transformant was further transformed with pSTVDLP1, followed by screening using 30 µl/ml chloramphenicol and 50 µg/ml ampicillin, whereby *E. coli* DH5α (pSTVDLP1, pBSDPS) harboring both of the vectors was obtained.

EXAMPLE 5

Using the base sequence of the human decaprenyl diphosphate synthase gene appearing on a Genbank database, PCR primers, hDPS1-N (SEQ ID NO:15) and hDPS1-C (SEQ ID NO:16), were prepared. Using a human liver cDNA library (cDNA Library, Human Liver, plasmid type (product of Takara Shuzo)) as a template, PCR was carried out by 2 minutes of heat treatment at 94° C. followed by 35 repetitions of the following cycle: one minute at 94° C.→one minute at 56° C.→two minutes at 72° C. The thus-amplified DNA was analyzed by 0.7% agarose gel electrophoresis.

The thus-obtained fragment of about 1,250 bp was excised from the gel, purified using a DNA extraction kit (Sephaglas (trademark) BandPrep Kit, product of Amersham Pharmacia Biotech) and then cloned in a vector for expression in *Escherichia coli* using a PCR product direct cloning kit (pT7BlueT-Vector Kit, product of NOVAGEN) to give pT7-hDPS1. The DNA base sequence was determined using a DNA sequencer (model 377, product of Perkin Elmer) and a DNA sequencing kit (product of Perkin Elmer, ABI PRISM (trademark) BigDye (trademark) Terminator Cycle Sequence Ready Reaction Kit with AmpliTaq (registered trademark) DNA polymerase, FS) and conducting the reactions according to the manual attached to the kit. As a result, the full-length sequence occurring on the database could be obtained.

pT7-hDPS1 was cleaved with the restriction enzymes SalI and BamHI (products of Takara Shuzo), followed by 0.8% agarose gel electrophoresis. The fragment of about 1,250 bp was excised from the gel and purified using a DNA extraction kit (Sephaglas (trademark) BandPrep Kit, product of Amersham Pharmacia Biotech), and this DNA fragment was then inserted into pUC119 (product of Takara Shuzo) at the SalI-BamHI site. The DNA base sequence was determined using a DNA sequencer (model 377, product of Perkin Elmer) and a DNA sequencing kit (product of Perkin Elmer, ABI PRISM (trademark) BigDye (trademark) Terminator Cycle Sequence Ready Reaction Kit with AmpliTaq (registered trademark) DNA polymerase, FS) and conducting the reactions according to the manual attached to the kit. As a result, an expression vector, pUhDPS1, could be obtained. *Escherichia coli* DH5α was transformed with this vector to give *E. coli* DH5α(pUh-DPS1).

EXAMPLE 6

Using the base sequence of the murine solanesyl diphosphate synthase gene appearing on a Genbank database, PCR primers, mSDS-N (SEQ ID NO:17) and mSDS-C (SEQ ID NO:18), were prepared. Using a murine liver cDNA library (CDNA Library, Mouse Liver, plasmid type (product of Takara Shuzo)) as a template, PCR was carried out by 2 minutes of heat treatment at 94° C. followed by 35 repetitions of the following cycle: one minute at 94° C.→one minute at 56° C.→two minutes at 72° C. The thus-amplified DNA was analyzed by 0.7% agarose gel electrophoresis.

The thus-obtained fragment of about 1,230 bp was excised from the gel, purified using a DNA extraction kit (Sephaglas (trademark) BandPrep Kit, product of Amersham Pharmacia Biotech) and then cloned in a vector for expression in *Escherichia coli* using a PCR product direct cloning kit (pT7BlueT-Vector Kit, product of NOVAGEN) to give pT7-mSDS. The DNA base sequence was determined using a DNA sequencer (model 377, product of Perkin Elmer) and a DNA sequencing kit (product of Perkin Elmer, ABI PRISM (trademark) BigDye (trademark) Terminator Cycle Sequence Ready Reaction Kit with AmpliTaq (registered trademark) DNA polymerase, FS) and conducting the reactions according to the manual attached to the kit. As a result, the full-length sequence occurring on the database could be obtained.

pT7-mSDS was cleaved with the restriction enzymes EcoRI and SalI (products of Takara Shuzo), followed by 0.8% agarose gel electrophoresis. The fragment of about 1,230 bp was excised from the gel and purified using a DNA extraction kit (Sephaglas (trademark) BandPrep Kit, product of Amersham Pharmacia Biotech), and this DNA fragment was then inserted into pBluescript II SK (+) (product of Toyobo) at the EcoRI-SalI site. The DNA base sequence was determined using a DNA sequencer (model 377, product of Perkin Elmer)

and a DNA sequencing kit (product of Perkin Elmer, ABI PRISM (trademark) BigDye (trademark) Terminator Cycle Sequence Ready Reaction Kit with AmpliTaq (registered trademark) DNA polymerase, FS) and conducting the reactions according to the manual attached to the kit. As a result, an expression vector, pBmSDS1, could be obtained. *Escherichia coli* DH5α was transformed with this vector to give *E. coli* DH5α(pBmSDS1l).

EXAMPLE 7

The transformants *E. coli* DH5α(pBSDPS), *E. coli* DH5α (pUhDPS1), and *E. coli* DH5α(pBmSDS1) resulting from transformation with the long-chain prenyl diphosphate synthase expression vectors constructed in Examples 4 to 6 were further transformed in various combinations with the expression vectors for activity elevatory protein expression as constructed in Examples 1 to 3.

For example, the transformant *E. coli* DH5α(pBSDPS) was further transformed with pSTVDLP1, as described in Example 4, to give the transformant *E. coli* DH5α (pSTVDLP1, pBSDPS) harboring both of the vectors. The following transformants were further obtained in the same manner:

The strain *E. coli* DH5α(pSTVDLP1, pUhDPS1) resulting from transformation with pSTVDLP1 and pUhDPS1;

The strain *E. coli* DH5α(pSTVDLP1, pBmSDS1) resulting from transformation with pSTVDLP1 and pBmSDS1;

The strain *E. coli* DH5α(pSTVK28-mDLP1, pUhDPS1) resulting from transformation with pSTVK28-mDLP1 and pUhDPS1;

The strain *E. coli* DH5α(pSTVK28-mDLP1, pBmSDS1) resulting from transformation with pSTVK28-mDLP1 and pBmSDS1;

The strain *E. coli* DH5α(pSTVK28-hDLP1, pUhDPS1) resulting from transformation with pSTVK28-hDLP1 and pUhDPS1; and The strain *E. coli* DH5α(pSTVK28-hDLP1, pBmSDS1) resulting from transformation with pSTVK28-hDLP1 and pBmSDS1.

Among them, *E. coli* DH5α(pSTVDLP1, pBSDPS) has been deposited with the National Institute of Advanced Industrial Science and Technology International Patent Organism Depositary, Central 6, 1-1-1 Higashi, Tsukuba, Ibaraki, Japan as of Apr. 17, 2001 under the accession number FERM BP-7548,

*E. coli* DH5α(pSTVDLP1, pUhDPS1) as of Apr. 19, 2002 under the accession number FERM BP-8025,

*E. coli* DH5α(pSTVK28-mDLP1, pBmSDS1) as of Apr. 19, 2002 under the accession number FERM BP-8027, and

*E. coli* DH5α(pSTVK28-hDLP1, pUhDPS1) as of April 19, 2002 under the accession number FERM BP-8026.

EXAMPLE 8

The transformants *E. coli* DH5α(pBSDPS), *E. coli* DH5α (pUhDPS1) and *E. coli* DH5α(pBmSDS1) obtained in the above examples were each shake-cultured overnight at 37° C. in 200 ml of LB medium containing 50 μg/ml ampicillin,

*E. coli* DH5α(pSTVDLP1) in 200 ml of LB medium containing 30 μg/ml chloramphenicol,

*E. coli* DH5α(pSTVK28-hDLP1) and *E. coli* DH5α (pSTVK28-mDLP1) each in 200 ml of LB medium containing 50 μg/ml kanamycin,

*E. coli* DH5α(pSTVDLP1, PBSDPS), *E. coli* DH5α (pSTVDLP1, pUhDPS1) and *E. coli* DH5α(pSTVDLP1, pBmSDS1) each in 200 ml of LB medium containing 30 μg/ml chloramphenicol and 50 μg/ml ampicillin,

*E. coli* DH5α(pSTVK28-hDLP1, pUhDPS1), *E. coli* DH5α (pSTVK28-hDLP1, pBmSDS1), *E. coli* DH5α(pSTVK28-mDLP1, pUhDPS1) and *E. coli* DH5α(pSTVK28-mDLP1, pBmSDS1) each in 200 ml of LB medium containing 50 μg/ml kanamycin and 50 μg/ml ampicillin. Bacterial cells were harvested by centrifugation (3,000 rpm, 20 minutes).

Acetone-methanol (7:2) (3 ml) was added to these cells, and extraction was effected by 6 repetitions of 30 seconds of sonication and the subsequent 30 seconds of standing on ice. Centrifugation (3,000 rpm, 5 minutes) gave an extract. This extract was vacuum-dried, 1 ml of chloroform-methanol (1:1) and an equal amount of a 0.7% aqueous solution of sodium chloride were added to the dried product, and the mixture was stirred well for attaining dissolution and then centrifuged at 14,000 rpm for 1 minute. The lower layer was extracted and dried, and the residue was dissolved in 50 μl of chloroform-methanol (2:1). This sample was spotted on a TLC plate, and developed with 100% benzene. The silica gel portion at approximately the same position as the spot obtained by development of coenzyme $Q_{10}$ as a standard was scraped off and extracted with 400 μl of chloroform-methanol (1:1). A 20-μl portion of this extract was analyzed by high-performance liquid chromatography (LC-10 A, product of Shimadzu). For the separation, a reversed phase column (YMC-pack ODS-A, 250×4.6 mm, S-5 μm, 120 A) was used, separation was effected using 100% ethanol as a mobile phase solvent, and the products coenzyme $Q_9$ and $Q_{10}$ were detected based on the absorbance at the wavelength 275 nm. The results are shown in FIGS. 4 to 8. As shown in FIGS. 4 to 8, it was revealed that the introduction of each DLP1 gene together with the prenyl diphosphate synthase gene and the subsequent expression thereof resulted in the production of coenzyme $Q_9$ and/or $Q_{10}$, which cannot be expressed in those *Escherichia coli* strains resulting from transformation with the prenyl diphosphate synthase gene alone.

INDUSTRIAL APPLICABILITY

The invention provides a protein involved in the expression of a eukaryotes-derived long-chain prenyl diphosphate synthase, a gene coding for such enzyme, a vector containing such enzyme gene, a transformant resulting from transformation with such vector and a long-chain prenyl diphosphate synthase gene-containing expression vector as well as a method of producing a long-chain prenyl diphosphate synthase (in particular decaprenyl diphosphate synthase and solanesyl diphosphate synthase) and of a coenzyme Q having a long-chain isoprenoid in its side chain (in particular coenzyme $Q_9$ or coenzyme $Q_{10}$). According to the invention, it is possible to produce eukaryote-derived enzymes as well as coenzyme $Q_9$, coenzyme $Q_{10}$ and the like.

The invention claimed is:

1. A transformant resulting from transformation of a host microorganism with a DNA, the DNA having the nucleotide sequence of SEQ ID NO: 3 and encoding a protein enabling or enhancing the activity of a protein encoded by the *Schizosaccharomyces pombe* DPS1 gene amplifiable with PCR primers of SEQ ID NOS: 13 and 14, the human DPS1 gene amplifiable with PCR primers of SEQ ID NOS: 15 and 16 and/or the mouse DPS1 gene amplifiable with PCR primers of SEQ ID NOS: 17 and 18 in the host microorganism; or the DNA having the nucleotide sequence isolated from the nucleotide sequence of SEQ ID NO: 3 by deletion, addition, insertion and/or substitution of one nucleotide thereof and encoding a protein enabling or enhancing the activity of a protein encoded by the *Schizosaccharomyces pombe* DPS1 gene amplifiable with PCR primers of SEQ ID NOS: 13 and 14, the human DPS1 gene amplifiable with PCR primers of SEQ ID NOS: 15 and 16 and/or the mouse DPS1 gene amplifiable with PCR primers of SEQ ID NOS: 17 and 18 in the host microorganism, wherein the transformant is transformed with the *Schizosaccharomyces pombe* DPS1 gene amplifiable with PCR primers of SEQ ID NOS: 13 and 14, the human DPS1 gene amplifiable with PCR primers of SEQ ID NOS: 15 and 16 and/or the mouse DPS1 gene amplifiable with PCR primers of SEQ ID NOS: 17 and 18 further introduced therein.

2. The transformant according to claim 1, the transformant being *E. coli* DH5α(pSTVK28-hDLP1, pUhDPS1) (FERM BP-8026).

3. The transformant according to claim 1, the transformant being *E. coli* DH5α(pSTVK28-hDLP1, pBmSDS 1).

4. A method of producing coenzyme Q comprising cultivating the transformant according to claim 1, 2, or 3 in a medium to cause formation and accumulation of a coenzyme Q in the culture, and recovering the coenzyme Q from the culture, wherein the host microorganism is *Escherichia coil*.

5. A transformant resulting from transformation of a host microorganism with an expression vector resulting from insertion of a DNA into a vector for expression, the DNA having the nucleotide sequence of SEQ ID NO: 3 and encoding a protein enabling or enhancing the activity of a protein encoded by the *Schizosaccharomyces pombe* DPS1 gene amplifiable with PCR primers of SEQ ID NOS: 13 and 14, the human DPS1 gene amplifiable with PCR primers of SEQ ID NOS: 15 and 16 and/or the mouse DPS1 gene amplifiable with PCR primers of SEQ ID NOS: 17 and 18 in the host microorganism; or the DNA having the nucleotide sequence isolated from the nucleotide sequence of SEQ ID NO: 3 by deletion, addition, insertion and/or substitution of one nucleotide thereof and encoding a protein enabling or enhancing the activity of a protein encoded by the *Schizosaccharomyces pombe* DPS1 gene amplifiable with PCR primers of SEQ ID NOS: 13 and 14, the human DPS1 gene amplifiable with PCR primers of SEQ ID NOS: 15 and 16 and/or the mouse DPS1 gene amplifiable with PCR primers of SEQ ID NOS: 17 and 18 in the host microorganism, the vector for expression being pSTV28 or pSTVK28-hDLP1, wherein the transformant is transformed with the *Schizosaccharomyces pombe* DPS1 gene amplifiable with PCR primers of SEQ ID NOS: 13 and 14, the human DPS1 gene amplifiable with PCR primers of SEQ ID NOS: 15 and 16 and/or the mouse DPS1 gene amplifiable with PCR primers of SEQ ID NOS: 17 and 18 further introduced therein.

6. A transformant resulting from transformation of *Escherichia coil* host microorganism with a DNA, the DNA having the nucleotide sequence of SEQ ID NO: 3 and encoding a protein enabling or enhancing the activity of a protein encoded by the *Schizosaccharomyces pombe* DPS1 gene amplifiable with PCR primers of SEQ ID NOS: 13 and 14, the human DPS1 gene amplifiable with PCR primers of SEQ ID NOS: 15 and 16 and/or the mouse DPS1 gene amplifiable with PCR primers of SEQ ID NOS: 17 and 18 in the host microorganism; or the DNA having the nucleotide sequence isolated from the nucleotide sequence of SEQ ID NO: 3 by deletion, addition, insertion and/or substitution of one nucleotide thereof and encoding a protein enabling or enhancing the activity of a protein encoded by the *Schizosaccharomyces pombe* DPS1 gene amplifiable with PCR primers of SEQ ID NOS: 13 and 14, the human DPS1 gene amplifiable with PCR primers of SEQ ID NOS: 15 and 16 and/or the mouse DPS1 gene amplifiable with PCR primers of SEQ ID NOS: 17 and 18 in the host microorganism, wherein the transformant is transformed with the *Schizosaccharomyces pombe* DPS1 gene amplifiable with PCR primers of SEQ ID NOS: 13 and 14, the human DPS1 gene amplifiable with PCR primers of SEQ ID NOS: 15 and 16 and/or the mouse DPS1 gene amplifiable with PCR primers of SEQ ID NOS: 17 and 18 further introduced therein.

7. The transformant according to claim 6, the transformant being *E. coli* DH5α(pSTVK28-hDLP1).

* * * * *